US 6,733,446 B2

(12) United States Patent
Lebel et al.

(10) Patent No.: US 6,733,446 B2
(45) Date of Patent: May 11, 2004

(54) AMBULATORY MEDICAL APPARATUS AND METHOD USING A TELEMETRY SYSTEM WITH PREDEFINED RECEPTION LISTENING PERIODS

(75) Inventors: Ronald J. Lebel, Sherman Oaks, CA (US); Varaz Shahmirian, Northridge, CA (US); John C. Gord, Venice, CA (US); John T. Armstrong, Pasadena, CA (US); John D. Richert, La Habra Heights, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 495 days.

(21) Appl. No.: 09/768,042

(22) Filed: Jan. 22, 2001

(65) Prior Publication Data

US 2003/0028080 A1 Feb. 6, 2003

Related U.S. Application Data

(60) Provisional application No. 60/177,414, filed on Jan. 21, 2000.

(51) Int. Cl.$^7$ .............................. A01B 5/00; G08B 23/00
(52) U.S. Cl. ..................................... 600/300; 340/573.1
(58) Field of Search ................................ 600/300, 301, 600/302, 303, 304, 305, 306, 307, 308, 309; 424/2; 340/573.1, 57.2, 573.3; 417/234, 235

(56) References Cited

U.S. PATENT DOCUMENTS

| 4,191,181 A | 3/1980 | Franetzki et al. |
| 4,217,894 A | 8/1980 | Franetzki |
| 4,270,532 A | 6/1981 | Franetzki et al. |
| 4,282,872 A | 8/1981 | Franetzki et al. |
| 4,373,527 A | 2/1983 | Fischell |
| 4,484,987 A | 11/1984 | Gough |
| 4,494,950 A | 1/1985 | Fischell |
| 4,511,355 A | 4/1985 | Franetzki et al. |
| 4,525,165 A | 6/1985 | Fischell |
| 4,559,037 A | 12/1985 | Franetzki et al. |
| 4,573,994 A | 3/1986 | Fischell |
| 4,594,058 A | 6/1986 | Fischell |
| 4,608,993 A | * 9/1986 | Albert ........................ 600/457 |
| 4,619,653 A | 10/1986 | Fischell |
| 4,627,906 A | 12/1986 | Gough |
| 4,661,097 A | 4/1987 | Fischell |
| 4,671,288 A | 6/1987 | Gough |

(List continued on next page.)

FOREIGN PATENT DOCUMENTS

| WO | WO 95/02426 | 1/1995 |
| WO | WO 96/03168 | 2/1996 |
| WO | WO00/74751 | 12/2000 |

Primary Examiner—Daniel Robinson
(74) Attorney, Agent, or Firm—Foley & Lardner

(57) ABSTRACT

An implanted medical device (e.g. infusion pump) and an external device communicate with one another via telemetry messages that are receivable only during windows or listening periods. Each listening period is open for a prescribed period of time and is spaced from successive listening periods by an interval. The prescribed period of time is typically kept small to minimize power consumption. To increase likelihood of successful communication, the window may be forced to an open state, by use of an attention signal, in anticipation of an incoming message. To further minimize power consumption, it is desirable to minimize use of extended attention signals, which is accomplished by the transmitter maintaining an estimate of listening period start times and attempting to send messages only during listening periods. In the communication device, the estimate is updated as a result of information obtained with the reception of each message from the medical device.

17 Claims, 5 Drawing Sheets

U.S. PATENT DOCUMENTS

| | | |
|---|---|---|
| 4,703,756 A | 11/1987 | Gough et al. |
| 4,731,051 A | 3/1988 | Fischell |
| 4,776,842 A | 10/1988 | Franetzki et al. |
| 4,781,798 A | 11/1988 | Gough |
| 4,784,645 A | 11/1988 | Fischell |
| 5,127,404 A | 7/1992 | Wyborny et al. |
| 5,191,326 A | 3/1993 | Montgomery |
| 5,193,539 A | 3/1993 | Schulman et al. |
| 5,193,540 A | 3/1993 | Schulman et al. |
| 5,358,514 A | 10/1994 | Schulman et al. |
| 5,368,562 A | 11/1994 | Blomquist et al. |
| 5,416,695 A | 5/1995 | Stutman et al. |
| 5,438,621 A | 8/1995 | Hornak et al. |
| 5,456,692 A | 10/1995 | Smith et al. |
| 5,497,772 A | 3/1996 | Schulman et al. |
| 5,559,828 A | 9/1996 | Armstrong et al. |
| 5,571,148 A | 11/1996 | Loeb et al. |
| 5,630,710 A | 5/1997 | Tune et al. |
| 5,647,854 A | 7/1997 | Olsen et al. |
| 5,651,767 A | 7/1997 | Schulman et al. |
| 5,658,133 A | 8/1997 | Anderson et al. |
| 5,658,250 A | 8/1997 | Blomquist et al. |
| 5,659,299 A | 8/1997 | Williamson et al. |
| 5,669,877 A | 9/1997 | Blomquist |
| 5,695,473 A | 12/1997 | Olsen |
| 5,718,234 A | 2/1998 | Warden et al. |
| 5,750,926 A | 5/1998 | Schulman et al. |
| 5,788,669 A | 8/1998 | Peterson |
| 5,810,771 A | 9/1998 | Blomquist |
| 5,876,370 A | 3/1999 | Blomquist |
| 5,917,346 A | 6/1999 | Gord et al. |
| 5,935,099 A | 8/1999 | Peterson et al. |
| 5,935,106 A | 8/1999 | Olsen |
| 5,957,958 A | 9/1999 | Schulman et al. |
| 5,999,848 A | 12/1999 | Gord et al. |
| 5,999,849 A | 12/1999 | Gord et al. |
| 6,024,539 A | 2/2000 | Blomquist |
| 6,026,124 A | 2/2000 | Lee et al. |
| 6,043,437 A | 3/2000 | Schulman et al. |
| 6,081,736 A | 6/2000 | Colvin et al. |
| 6,088,608 A | 7/2000 | Schulman et al. |
| 6,119,028 A | 9/2000 | Schulman et al. |
| 6,123,686 A | 9/2000 | Olsen et al. |
| 6,190,324 B1 * | 2/2001 | Kieval et al. ............... 600/483 |
| 6,248,080 B1 * | 6/2001 | Miesel et al. ............... 600/561 |
| 6,400,987 B1 * | 6/2002 | Garberoglio ................. 607/18 |
| 6,406,426 B1 * | 6/2002 | Reuss et al. ................. 600/300 |
| 6,450,953 B1 * | 9/2002 | Place et al. ................. 600/300 |

* cited by examiner

AMBULATORY MEDICAL APPARATUS AND METHOD USING A TELEMETRY SYSTEM WITH PREDEFINED RECEPTION LISTENING PERIODS

RELATED APPLICATIONS

This application claims the benefit of prior filed U.S. Provisional Patent Application No. 60/177,414; filed Jan. 21, 2000, by Ronald J. Lebel, et al., and entitled "Medical Apparatus and Method Including an Implantable Device and an External Communication Device". The entirety of this provisional application is hereby incorporated herein by this reference, including appendices filed therewith and any references incorporated therein by reference, as if set forth in full herein.

FIELD OF THE DISCLOSURE

This invention relates generally to ambulatory medical systems that include a medical device and a control device that communicate via telemetry and that initiate message reception during predefined listening periods. Preferred embodiments relate to implantable infusion pumps and external devices for communicating therewith.

BACKGROUND

Various ambulatory medical devices have been proposed and a number of such devices are commercially available. These devices include, for example, implantable infusion pumps, externally carried infusion pumps, implantable pacemakers, implantable defibrillators, implantable neural stimulators, implantable physiological sensors, externally carried physiologic sensors, and the like.

As appropriate operation of ambulatory medical devices may be critical to those patients being treated using those devices, and as telemetry communications between ambulatory medical devices and controllers can greatly enhance the convenience of using such devices, or even be an enabling necessity to the use of such devices (e.g. implantable devices with sophisticated functionality), the operation of such medical devices can benefit significantly by use of telemetry systems and protocols that have features/elements that lead to optimization of various attributes Such attributes may include (1) flexibility in communicating the wide variety signals that may be useful to controlling and retrieving information from a sophisticated medical device, (2) robustness in distinguishing actual signals from noise, (3) robustness in distinguishing valid signals from corrupt signals, (4) robustness in ascertaining when appropriate communication has occurred and when additional communication must be attempted, (5) a reasonable efficiency in communication time, and/or (6) a reasonable efficiency in electrical power consumption associated with conveying information over the telemetry system.

Implantable medical devices typically operate by battery power. The batteries may or may not be rechargeable. Higher consumption of power from an implantable medical device containing non-rechargeable batteries leads to a shortening of the usable life of the device and an associated increased frequency of surgery, potential pain, recovery, and inconvenience. Higher consumption of power from an implantable medical device containing rechargeable batteries leads to more frequent charging periods for the batteries and associated inconvenience and may lead to an overall shortening of the usable life of the device. As such, whether or not an implantable medical device contains rechargeable batteries or non-rechargeable batteries, it is desirable to lower the power consumption of the device. As telemetry reception and transmission are highly energy consumptive, it is desirable to minimize the operation time of telemetry reception and transmission modules.

A telemetry reception module of a first device needs to (1) be powered to listen for potential incoming messages from a second device, (2) stay powered during the entire receipt of the message, and (3) potentially be powered one or more repeated times to receive a duplicate message when the second device is expecting a response to its original message and does not receive one. A telemetry transmission module of a first device needs to (1) be powered so it can transmit a desired message to a second device, and (2) potentially be powered one or more times to retransmit a duplicate message when the first device fails to receive confirmation that original message was received by the second device.

A need exists in the field for improved telemetry features/elements that tend to minimize one or both of power on time for telemetry reception modules and/or telemetry transmission modules to reduce power drain on batteries used in powering ambulatory medical devices and communicators. A need exists in the field to ensure that device users are not inconvenienced with long delay times that may be associated with inputting information into the communication device, transmitting information via telemetry to the medical device, and waiting for confirmation that the transmitted information was appropriately received and is was or will be appropriately acted upon.

SUMMARY OF THE INVENTION

It is a first object of certain aspects of the invention to reduce power consumption in an ambulatory medical system associated with receiving messages via telemetry.

It is a second object of certain aspects of the invention to reduce power consumption in an ambulatory medical system associated with transmitting messages via telemetry.

It is a third object of certain aspects of the invention to shift power consumption burdens associated with telemetry activities away from an implantable medical device to an external communication device.

It is a fourth object of certain aspects of the invention to achieve enhanced synchronization between timers in the medical device and in the communication device than is inherently achieved based on frequency oscillation tolerance differences allowed in the principle oscillators used in the two devices.

Other objects and advantages of various aspects of the invention will be apparent to those of skill in the art upon review of the teachings herein. The various aspects of the invention set forth below as well as other aspects of the invention not specifically set forth below but ascertained from the teachings found herein, may address the above noted objects or other objects ascertained from the teachings herein individually or in various combinations. As such, it is intended that each aspect of the invention address at least one of the above noted objects or address some other object that will be apparent to one of skill in the art from a review of the teachings herein. It is not intended that all, or even a portion of these objects, necessarily be addressed by any single aspect of the invention even though that may be the case with regard to some aspects.

It is a first aspect of the invention to provide a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the CD telemetry system listens during preselected outbound listening periods for at least a selected type of message from the MD telemetry system.

In a specific variation of the first aspect of the invention, the medical device is capable of initiating communication with the communication during outbound listening periods, and the communication device additionally includes (a) a CD clock system; (b) CD monitoring system that monitors a CD time, based on the CD clock system, that corresponds to a selected portion of a message received by the CD telemetry system from the MD telemetry system; and (c) a CD control system for effectively comparing the CD time to an anticipated outbound transmission start time by the MD telemetry system for that selected portion of the message to adaptively adjust a subsequent outbound listening period based, at least in part, on the comparison of the CD time to the anticipated outbound transmission start time.

In another variation of the first aspect of the invention, the MD telemetry system activates a window for receiving messages from the CD telemetry system during prescribed inbound listening periods and wherein successive prescribed inbound listening periods are separated by a smaller interval than an interval that separates successive outbound listening periods.

A second aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the CD telemetry system does not send out a message as the message is generated but instead delays the sending out of a message until a next prescribed inbound transmission start time occurs.

A third aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the MD telemetry system listens for any messages coming from the CD telemetry system beginning at prescribed inbound listening start times for prescribed inbound listening periods.

In a specific variation of the third aspect of the invention, the communication device attempts to anticipate the prescribed inbound listening periods and sets inbound transmission start times to correspond to the anticipated prescribed inbound listening periods.

In another specific variation of the third aspect of the invention, the prescribed inbound listening start times and prescribed inbound listening periods are determined and activated automatically without microprocessor intervention.

A fourth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the MD telemetry system and the CD telemetry send and receive messages using digital modulation and demodulation.

In a specific variation of the eleventh aspect of the invention the digital modulation and demodulation uses spread spectrum technology.

In another specific variation of the eleventh aspect of the invention, the MD telemetry system includes (1) a digital modulator, (2) a receiving amplifier, (3) a digital receiver, (4) a mixer, and (5) a low pass filter wherein at least two of (1)–(5) are combined into a single integrated circuit or where all of (1)–(5) are combined into no more than two integrated circuits.

A fifth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein at least one of the communication device or the medical device sets a preamble length, for at least some messages, as a function of at least the difference between a present time and a time of a previous communication.

In a specific variation of the fifth aspect of the invention, the estimated listening time is based, at least in part, on a time difference between the present time and a time of a previously received message. In a further variation, the communication device derives the estimate. In still a further variation a transmission time is based, at least in part, on a predefined desired transmission time as modified by an estimated amount of drift that may have occurred between a time base used by the medical device and a time base used by the communication device.

A sixth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein at least one of the communication device or the medical device determines an estimated listening time for the other of the communication device or the medical device and sets a transmission start time as a function of the estimated listening time.

A seventh aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device or the communication device comprises an oscillator circuit that produces a pulse stream that oscillates at an initial frequency that is greater than a desired frequency and wherein signals from the oscillator circuit are passed through circuitry that removes selected pulses from an input pulse stream such that a modified oscillator signal is produced having a modified pulse stream that oscillates with an average frequency closer to a desired frequency than the initial frequency.

In a specific variation of the seventh aspect of the invention, the circuitry comprises a counter that repetitively counts to a first predefined value and then removes a pulse from the initial pulse stream to produce the modified pulse stream. In a further variation, a timing signal is generated from the modified pulse stream by utilization of a counter that counts to a second predefined value and then outputs a pulse. In a further variation, the first predefined value is defined by software. In still a further variation, the first predefined value is subject to modification during a normal course of operation of the medical system. In still a further variation, the modification of the first predefined value causes the modified pulse stream to oscillate at a frequency closer to the desired frequency than it otherwise would if it remained unchanged. In still a further variation the modification of the first predefined value is at least in part based on a temperature of the oscillator circuit.

An eighth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein at least one of the medical device or the communication device periodically adjusts a concept of time to match at least in part a concept of time in the other of the communication device or the medical device.

In a specific variation of the eighth aspect of the invention, the concepts of time of the medical device and the communication device are used by each for controlling, at least in part, telemetry operations of the medical device and communication device, respectively.

In another specific variation of the eighth aspect of the invention, a first of the communication device or the medical device adjusts a first concept of time to match that of the second of the communication device or medical device, while the second of the medical device or the communication device matches a second concept of time to that of the first of the communication device or medical device.

A ninth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the communication device further comprises a CD timing module, a CD crystal oscillator, and at least one CD temperature transducer, and wherein the CD timing module uses at least the CD temperature transducer in combination with known properties of the CD crystal oscillator to modify a rate of tracking of time by the CD timing module.

In a specific variation of the ninth aspect of the invention, he modified time is used in transmitting messages to the medical device. In a further variation, the medical device listens only part of the time for incoming messages from the CD telemetry system or transmits unsolicited messages to the communication device only at selected times, and the communication device estimates the medical device's inbound listening times or potential outbound transmission times based, at least in part, upon at least one temperature measurement made since a last message was exchanged between the medical device and the communication device in combination with known variations in crystal oscillation frequency with temperature.

A tenth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device further comprises an MD timing module, an MD crystal oscillator, and at least one MD temperature transducer, and wherein the MD timing module uses at least the MD temperature transducer in combination with known properties of the MD crystal oscillator to modify a rate of tracking of time by the MD timing module.

An eleventh aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the MD telemetry system is activated to enable reception or transmission of messages only a portion of the time.

A twelfth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device sends out unsolicited messages to the communication device.

A thirteenth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the medical device sends outbound messages to the communication device and the communication device receives outbound messages from the medical device; wherein the medical device receives inbound messages from the communication device and the communication device sends inbound messages to the medical device; wherein the medical device listens for inbound messages beginning at an inbound listening start time and continuing for an inbound listening period; wherein the communication device listens for outbound messages beginning at an outbound listening start time and continuing for an outbound listening period; wherein the medical device transmits outbound messages beginning at an outbound transmission start time and continues transmission of a selected portion of the outbound messages for an outbound transmission period; wherein the communication device transmits inbound messages beginning at an inbound transmission start time and continues transmission of a selected portion of the inbound messages for an inbound transmission period; wherein an interval exists between successive inbound listening periods; wherein an interval exists between successive outbound listening periods; and wherein at least a selected one of (1) or (2) occurs: (1) at least one of the inbound transmission period or the outbound transmission period is extended after a failure to communicate occurs; or (2) at least one of the inbound transmission start times or outbound transmission start times undergoes a shift relative to an anticipated inbound listening start time or an anticipated outbound listening start time, respectively; and wherein after one or more extensions and/or one or more shifts, all portions of the interval between successive inbound or outbound listening periods would be broadcast to during inbound transmission periods or outbound transmission periods, respectively.

A fourteenth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein at least one of the MD telemetry system or the CD telemetry system is configured to establish frame synchronization and to confirm that a message is intended specifically for the medical device or the communication device, respectively, by confirming receipt of a predefined identifier.

A fifteenth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein a timing associated with a transmission of a message or reception of a message, by one of the medical device or the communication device is based, at least in part, on an estimate of the amount of drift in time that has occurred between a present time and a time of a previous synchronization of a timer in the medical device and a timer in the communication device.

A sixteenth aspect of the invention provides a medical system that includes (a) an ambulatory medical device (MD) that includes MD electronic control circuitry that further includes at least one MD telemetry system and at least one MD processor that controls, at least in part, operation of the MD telemetry system and operation of the medical device, wherein the medical device is configured to provide a treatment to a body of a patient or to monitor a selected state of the body; and (b) a communication device (CD) that includes CD electronic control circuitry that further includes at least one CD telemetry system and at least one CD processor that controls, at least in part, operation of the CD telemetry system and operation of the communication device, wherein the CD telemetry system sends messages to or receives messages from the MD telemetry system, wherein the MD telemetry system does not send out a message as the message is generated but instead delays the sending out of a message until a next prescribed outbound transmission start time occurs.

Additional specific variations, provide the medical devices of each of the above aspects and above noted variations as implantable devices such as implantable infusion pumps, implantable physiological sensors, implantable stimulators, and the like, or external devices such subcutaneous delivery infusion pumps or sensors that ascertain a physiological parameter or parameters from subcutaneous tissue or from the skin of the patient. Such infusion pumps may dispense insulin, analgesics, neurological drugs, drugs for treating AIDS, drugs for treating chronic ailments or acute ailments. Sensors may be used to detect various physiological parameters such as hormone levels, insulin, pH, oxygen, other blood chemical constituent levels, and the like. The sensor may be of the electrochemical type, optical type, and may or may not be enzymatic in operation.

In even further variations of the above noted aspects, and above noted variations, one or more of the following is provided: (1) a first portion of the MD telemetry system is incorporated into the MD processor and a second portion of the MD telemetry system is external to the MD processor, (2) a first portion of the CD telemetry system is incorporated into the CD processor and a second portion of the CD telemetry system is external to the CD processor, (3) the MD processor includes an MD central processing unit and at least one other MD functional module, (4) the CD processor includes a CD central processing unit and at least one other CD functional module, (5) the MD electronic control circuitry includes at least one external MD functional module, other than a portion of the MD telemetry system, that is external to the MD processor, or (6) the CD electronic control circuitry includes at least one external CD functional module, other than a portion of the CD telemetry system, that is external to the CD processor.

Still additional aspects of the invention provide method counterparts to the above system aspects as well as to other functional associations and relationships, and processes that have not been specifically set forth above but will be understood by those of skill in the art from a review of the teachings provided herein.

Further aspects of the invention will be understood by those of skill in the art upon reviewing the teachings herein. These other aspects of the invention may provide various combinations of the aspects presented above as well as provide other configurations, structures, functional relationships, and processes that have not been specifically set forth above.

BRIEF DESCRIPTION OF THE DRAWINGS

The above referred to objects and aspects of the present invention will be further understood from a review of the description to follow, the accompanying drawings, and the claims set forth hereafter, wherein:

DETAILED DESCRIPTION OF PREFERRED EMBODIMENTS

Figure 1A:
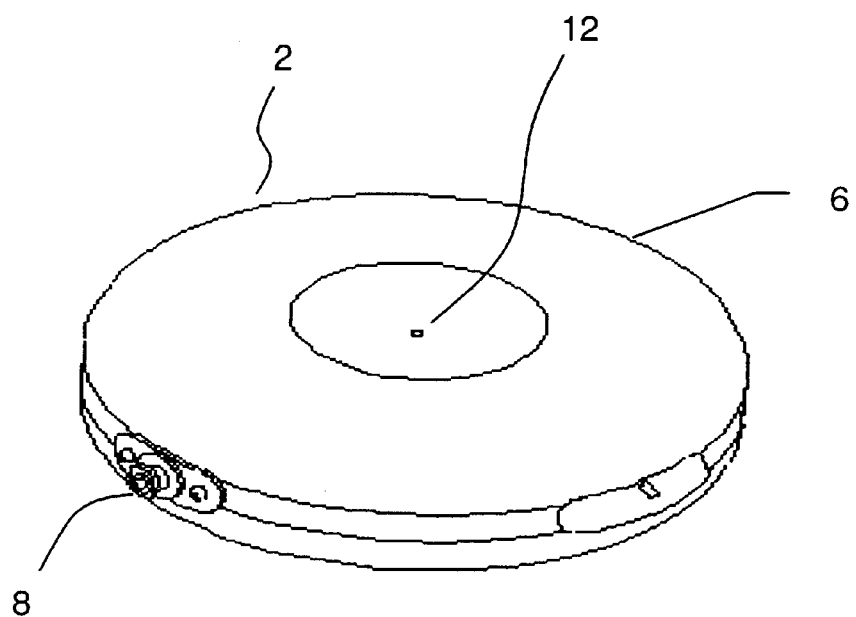
FIG. 1a depicts a perspective view of the main body of the implantable device of the first preferred embodiment.

Various details about the structural and functional configuration and operation of preferred ambulatory medical devices and preferred communication devices are found in several US patent applications filed concurrently herewith and incorporated herein by reference in their entireties: (1) Docket No. USP-1075-A, (2) Docket No. USP-1076-A, (3) Docket No. USP-1078-A, (4) Docket No. USP 1079-A, and (5) Docket No. USP-1080-A.

U.S. patent application Ser. No. To Be Determined, filed on Jan. 22, 2001 (concurrently herewith), by Starkweather, et al., entitled "Ambulatory Medical Apparatus and Method Having Telemetry Modifiable Control Software", corresponding to Medical Research Group, Inc. Docket No. USP-1075-A, is hereby incorporated herein by this reference as if set forth in full herein. This application provides teachings concerning an implantable medical device (e.g. infusion pump) and handheld communication device wherein the implantable device is capable of operating under control of different software programs, wherein a first program operates after resetting the implantable device and is not capable of allowing significant medical functionality but is capable of selected telemetry operations including telemetry operations that allow replacement software to be downloaded, and wherein a second program may be caused to take control of the device and enables medical functionality and selected telemetry operations but is incapable of receiving replacement software. It is also taught that a software image may be received in multiple messages where each message is provided with its own validation code and wherein a validation code for the whole image is provided and wherein each provided validation code must compared to a derived validation code prior to accepting the validity of the replacement software.

U.S. patent application Ser. No. To Be Determined, filed on Jan. 22, 2001 (concurrently herewith), by Lebel, et al., entitled "Ambulatory Medical Apparatus and Method Using a Robust Communication Protocol", corresponding to Medical Research Group, Inc. Docket No. USP-1076-A, is hereby incorporated herein by the references as if set forth in full herein. An implanted medical device (e.g. infusion pump) and external device communicate with one another via telemetry wherein messages are transmitted under a robust communication protocol. The communication protocol gives enhanced assurance concerning the integrity of messages that impact medical operations of the implantable device. Messages are transmitted using a multipart format that includes a preamble, a frame sync, a telemetry ID, data, and a validation code. The data portion of the message includes an op-code that dictates various other elements that form part of the message. The data portion may also include additional elements such as sequence numbers, bolus numbers, and duplicate data elements. A telemetry ID for the transmitting device may be implicitly embedded in the message as part of the validation code that is sent with the message and that must be pre-known by the receiver to confirm the integrity of the received message.

U.S. patent application Ser. No. To Be Determined, filed on Jan. 22, 2001 (concurrently herewith), by Lebel, et al., entitled "Ambulatory Medical Apparatus with Hand Held Communication Device", corresponding to Medical Research Group, Inc. Docket No. USP-1078-A, is hereby incorporated herein by this reference as if set forth in full herein. This application provides teachings concerning an implantable medical device (e.g. infusion pump) and handheld communication device (CD) that exchange messages via telemetry such that commands are supplied to the implantable device and operational information is obtained therefrom. The CD is controlled, at least in part, by a processor IC according to a software program operating therein and provides feedback to a user via a visual display, an audio alarm, and a vibrational alarm, and allows input from the user via a touch sensitive keypad. Certain input functions are restricted by password. The visual display includes an icon and fixed element display region and a bitmap display region. The fixed element display region includes time and date displays, battery and drug level displays that decrement, and a moving delivery state display. Various screens allow operational or log information to be displayed and/or user entry of commands. Program features when disable are removed from a series of screen options that can be scrolled through.

U.S. patent application Ser. No. To Be Determined, filed on Jan. 22, 2001 (concurrently herewith), by Starkweather, et al., entitled "Method and Apparatus for Communicating Between an Ambulatory Medical Device and Control Device Via Telemetry Using Randomized Data", corresponding to Medical Research Group, Inc. Docket No. USP-1079-A, is hereby incorporated herein by this reference as if set forth in full herein. This application provides teachings concerning an implantable medical device (e.g. infusion pump) and handheld communication device that communicate with one another via telemetry wherein transmitted messages have enhanced numbers of and/or regularity of bit transitions to minimize the risk of synchronization loss between transmitted bits of data and received bits of data. It is taught that bit transitions for portions of messages may be enhanced by applying a pseudo-randomization scheme to those portions of messages that are transmitted in a way that allows the receiver to extract the original data from the received randomized data. Preferred randomization techniques modify (i.e. randomize) the data using a CRC value that is being accumulated while simultaneously causing the modified data to modify subsequent accumulation of the CRC itself. Upon reception, the reversal of data randomization is then made to occur so that the intended message is appropriately received.

U.S. patent application Ser. No. To Be Determined, filed on Jan. 22, 2001 (concurrently herewith), by Lebel, et al., entitled "Microprocessor Controlled Ambulatory Medical Apparatus with Hand Held Communication Device", corresponding to Medical Research Group, Inc. Docket No. USP-1080-A, is hereby incorporated herein by this reference as if set forth in full herein. This application provides teachings concerning an implantable medical device (e.g. infusion pump) and handheld communication device. wherein an implantable infusion pump possesses operational functionality that is, at least in part, controlled by software operating in two processor ICs which are configured to perform some different and some duplicate functions. The pump exchanges messages with the external communication device via telemetry. Each processor controls a different part of the drug infusion mechanism such that both processors must agree on the appropriateness of drug delivery for infusion to occur. Delivery accumulators are incremented and decremented with delivery requests and with deliveries made. When accumulated amounts reach or exceed, quantized deliverable amounts, infusion is made to occur. The accumulators are capable of being incremented by two or more independent types of delivery requests. Operational modes of the infusion device are changed automatically in view of various system errors that are trapped, various system alarm conditions that are detected, and when excess periods of time lapse between pump and external device interactions.

The first embodiment of the present invention provides a long term implantable medical delivery system that controllably supplies insulin to the body of a patient afflicted with diabetes mellitus. This embodiment includes an implantable medical device and an external communication device. In the most preferred embodiments, the communication device is a hand held device that is used directly by the patient to interact with the medical device as opposed to being limited to use by a physician, nurse, or technician. It is preferred that the communication device provide (1) the ability to send commands to the medical device, (2) receive information from the medical device, and (3) be able to present to the patient at least a portion of the information it receives from the medical device. In preferred embodiments, the patient interacts with the medical device via the communication device at least once per week, on average, more preferably at least once every other day, on average, and most preferably at least once per day, on average.

The implantable medical device (MD) includes a biocompatible housing; a reservoir within the housing for holding a quantity of insulin; a side port that attaches to the side of the housing, a catheter, that connects to the side port; a pumping mechanism, within the housing for moving the insulin from the reservoir through the sideport and through the catheter to the body of the patient; and control, monitoring, and communication electronics located within the housing. In alternative embodiments various portions of implantable medical device hardware may be located outside the housing. For example, the pumping mechanism or a telemetry antenna may be located within the sideport or other side mounted housing; or a telemetry antenna may mounted on the outside surface of the housing, or extend along the catheter The external communication device (CD) communicates commands to the medical device, receives information from the medical device, and communicates system status and system history to the patient. The external communication device includes a housing; a keypad mounted on the housing; a display forming part of the housing; and control, monitoring, and communication electronics located within the housing. In alternative embodiments, the keypad may be replaced in whole or in part by a touch sensitive display or a voice recognition system. In addition, or alternatively, the display may be replaced in whole or in part by a speech generation system or other audio communication system.

Figure 1B:
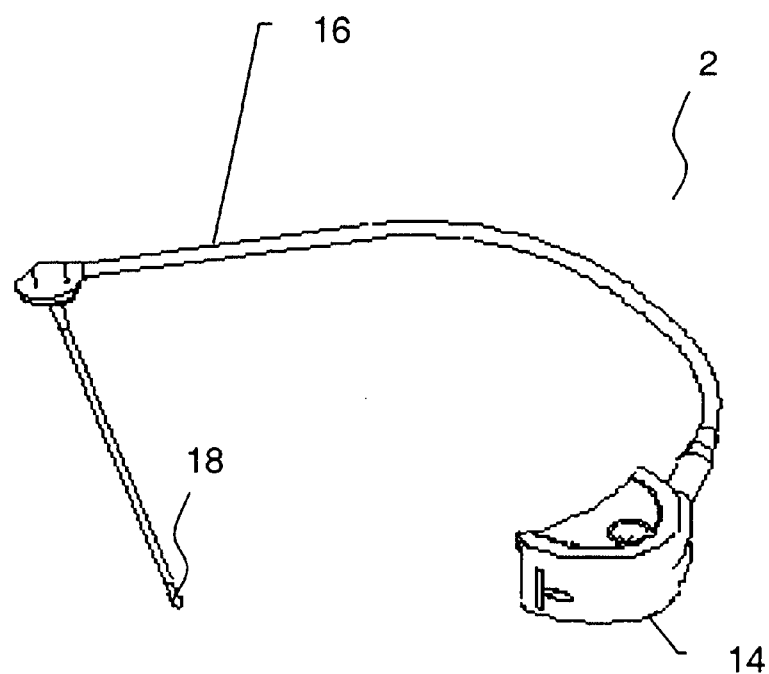
FIG. 1b depicts a perspective view of the support and catheter assembly that attaches to the main body of the implantable device of the first preferred embodiment.

The outer appearance of the implantable device 2 is depicted in two pieces in FIGS. 1a and 1b and includes housing 6 having a drug outlet port 8, and a refill port 12, a removable sideport 14 that mounts against the side of the housing 6 over outlet port 8, and a catheter 16 having a distal end 18 and a proximal end that attaches to sideport 14. In alternative embodiments, the implantable device may take on a different shape and/or the sideport may be removed in favor of a permanently mounted catheter assembly.

Figure 2:
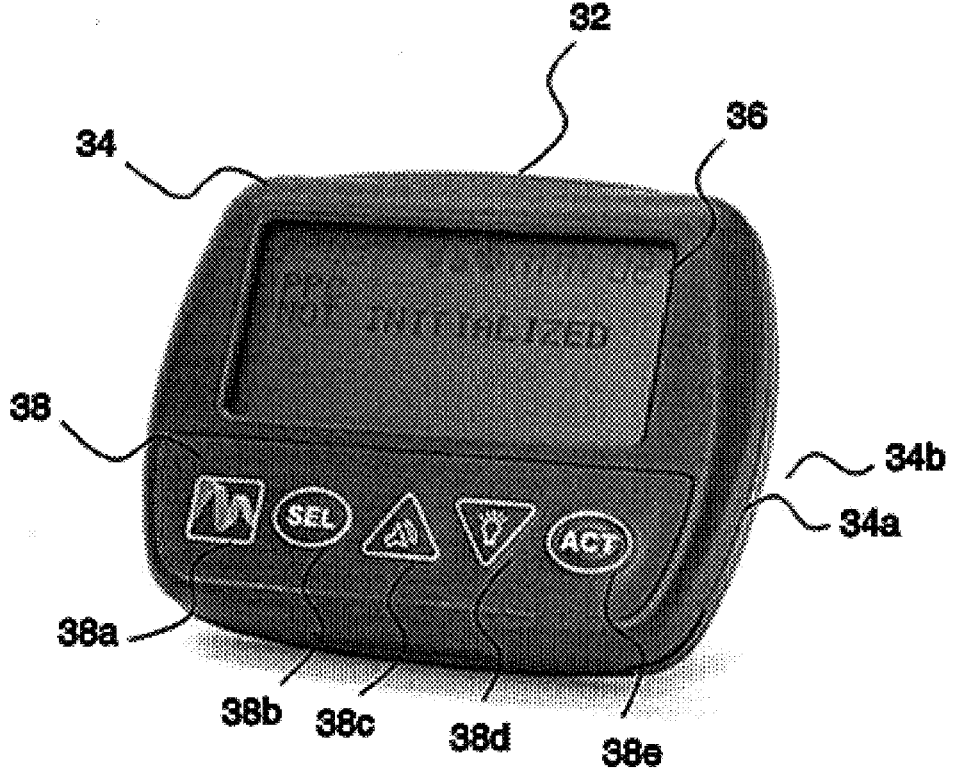
FIG. 2 depicts a perspective view of the external communication device of the first preferred embodiment.

The outer appearance of the external communication device 32 is depicted in FIG. 2. The various components of the external communication device are fitted in or on housing 34. Housing 34 is divided into a front portion 34a and a back portion 34b. The front portion 34a is provided with an opening in which an LCD panel 36 is positioned. The panel 36 has a lower portion that is a bit map display and an upper portion that provides icons and fixed element displays. The front portion 34a of the external communication device is also provided with a five-element keypad 38. A first key 38a is not located under a raised pad and does not provide tactile feedback when it is touched and may be used for special functions. The remaining four keys 38b, 38c, 38d, and 38e have raised pads that provide tactile feedback when they are depressed. These remaining keys may be used in normal device operation and are known as the select key, the up arrow key, down arrow key, and the activate key, respectively. The back portion 34b of the housing is fitted with a door under which a compartment is located for holding a replaceable battery.

Figure 3:
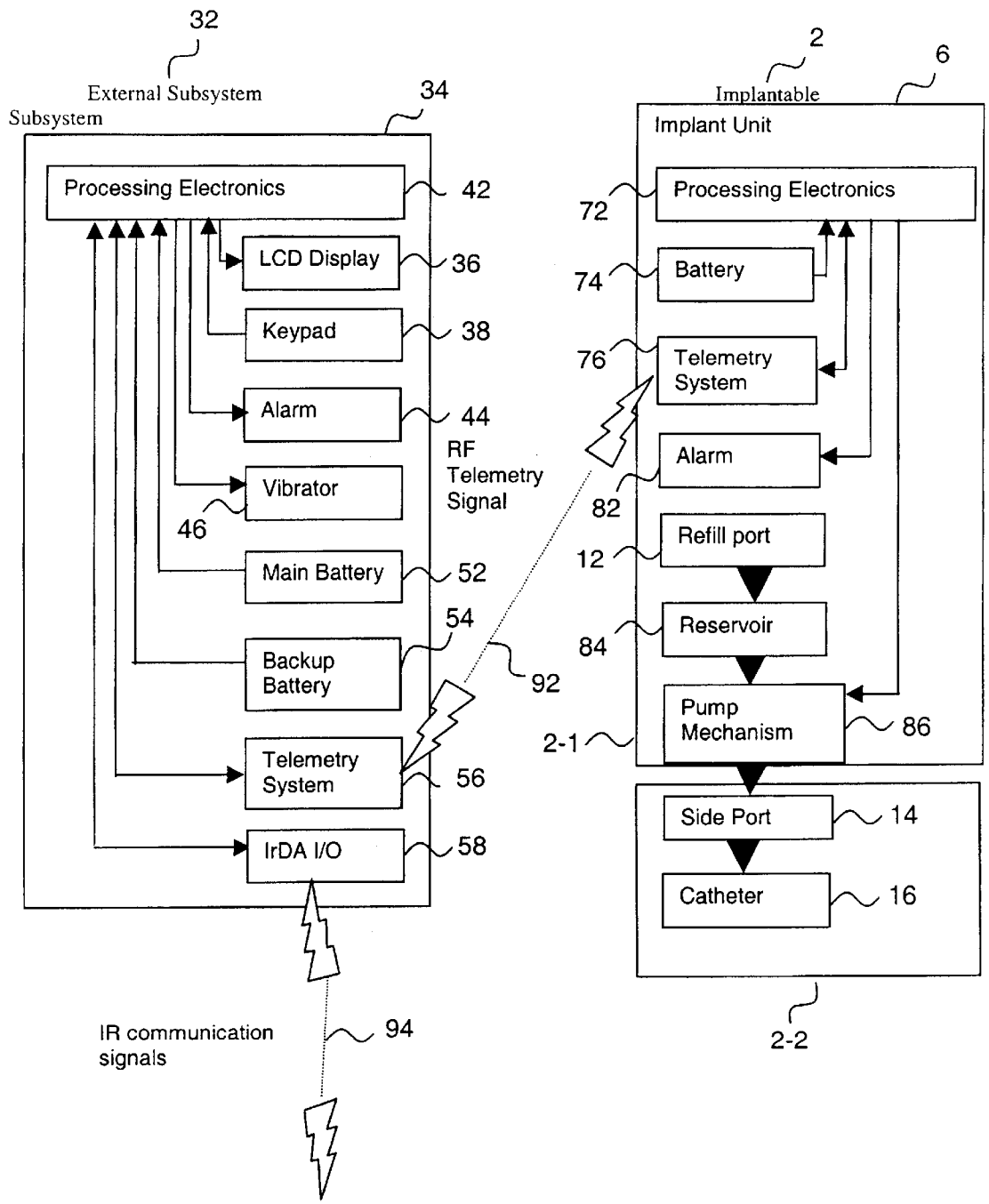
FIG. 3 depicts a block diagram of the main components/modules of both the implantable device and the external communication device of the first preferred embodiment.

FIG. 3 depicts a simplified block diagram of various functional components or modules (i.e. single components or groups of components) included in the implantable medical device 2 and external communication device 32. The external communication device 32 includes (1) a housing or cover 34 preferably formed from a durable plastic material, (2) processing electronics 42 including a CPU and memory elements for storing control programs and operation data, (3) an LCD display 36 for providing operation for information to the user, (4) a keypad 38 for taking input from the user, (5) an audio alarm 44 for providing information to the user, (6) a vibrator 46 for providing information to the user, (7) a main battery 52 for supplying power to the device, (8) a backup battery 54 to provide memory maintenance for the device, (9) a radio frequency (RF) telemetry system 56 for sending signals to the implantable medical device and for receiving signals from the implantable medical device, and (10) an infrared (IR) input/output system 58 for communicating with a second external device.

The second external device may include input, display and programming capabilities. The second device may include a personal computer operating specialized software. The computer may be used to manipulate the data retrieved from the communication device or the medical device or it may be used to program new parameters into the communication device or directly into the medical device, or even used to download new software to the communication device or to the medical device. The manipulation of the data may be used in generating graphical displays of the data to help aid in the interpretation of the data. Such data interpretation might be particularly useful if the medical device provides data concerning a physiological parameter of the body of the patient, such as a glucose level versus time. More particularly the computing power and display attributes of the second device might be even more useful when the medical device includes both an implanted sensor (e.g. glucose sensor), or external sensor, and an implanted pump (e.g. insulin pump), or external pump, where the second external device may be used to enhance the ability to ascertain the effectiveness of the two devices working together. Successful control periods and problem control periods could be more readily identified. In fact, if the two devices work on a closed loop basis or semi-closed loop basis, the analysis performable by the second external device may be useful in deriving new closed loop control parameters and/or in programming those parameters directly into the communication device or the medical device or devices.

The implantable device 2 includes (1) a housing or cover 6 preferably made of titanium that may or may not be coated to enhance biocompatibility, (2) processing electronics 72 including two CPUs and memory elements for storing control programs and operation data, (3) battery 74 for providing power to the system, (4) RF telemetry system 76 for sending communication signals (i.e. messages) to the external device and for receiving communication signals (i.e. messages) from the external device, (5) alarm or buzzer 82 for providing feedback to the user, (6) refill port 12 for accepting a new supply of drug as needed, (7) reservoir 84 for storing a drug for future infusion, (8) pumping mechanism 86 for forcing selected quantities of drug from the reservoir through the catheter to the body of the patient, (9) sideport 14 for providing a replaceable connection between the (10) catheter and the pump housing and for allowing diagnostic testing of the fluid handling system to occur, and catheter 16 for carrying medication from the implant location to the desired infusion location.

In this embodiment, the pump mechanism is preferably a low power, electromagnetically driven piston pump. Such as for example Model Nos. P650005 or P650009 as sold by Wilson Greatbatch Ltd. of Clarence, N.Y. which have stroke volumes of 0.5 microliters and draw under 7 mJ (e.g. about 6 mJ) per pump stroke and under 4 mJ (e.g. about 3 mJ) per pump stroke, respectively. The pump mechanism dispenses a sufficiently small volume of insulin per stroke so that a desired level of infusion resolution is achieved. For example if an infusion resolution of 0.2 units of insulin were desired when using U400 insulin, then a stroke volume of about 0.5 microliters would be appropriate. In other embodiments other types of infusion pumps may be used, e.g. peristaltic pumps.

The size of the reservoir is preferably large enough to hold sufficient insulin so that refilling does not have to occur too often. For example, it is preferred that time between refills be within the range of 1.5–4 months or longer, more preferably at least 2 months, and most preferably at least 3 months. Opposing the containment of a large volume of insulin, is the desire to keep the implantable device as small as possible. In the present embodiment the implantable device and reservoir has been designed to hold about 13 ml of insulin. A preferred insulin has a concentration of 400 units per milliliter and is available from Aventis HOE 21 Ph U-400 from Aventis Pharma (formerly Hoechst Marion Roussel AG, of Frankfurt am Main, Germany). This insulin is a highly purified, semi-synthetic human insulin with 0.2% phenol as a preserving agent, glycerol as an isotonic component, TRIS as a buffer, plus zinc and Genopal® as stabilizing agents. This quantity and insulin concentration allows about 2–4 months between refills. In other embodiments higher insulin concentrations may be used (e.g. U-500 or U-1000) to increase time between refills or to allow reduction in reservoir size. In some embodiments, when higher concentrations are used, any quantized minimum delivery amounts may be reduced by modifying the pumping mechanism, control circuitry, or software control algorithm so that infusion resolution is not adversely impacted.

The external communication device contains appropriate software to provide proper control of the device including appropriate functionality to allow communication with the medical device, to allow adequate control of the operation of the medical device, and to give appropriate feedback to the user regarding overall system operation. The medical device is provided with appropriate software to allow communication with the external communication device, to allow safe and appropriate operation of the medical functionality of the device, and to allow direct feedback to the user concerning device status via the internal alarm.

The control electronics of both the implantable device and external communication device are centered around microprocessor based integrated circuits, i.e. processor ICs, that are implemented in the present embodiment in the form of application specific integrated circuits (ASICs). In the present embodiment, the control electronics of the implantable device are centered around two identical ASICs that are mounted on a hybrid circuit board. Two such ASICs are used in the implantable device to increase operational safety of the device by configuring the device to require that the two ASICs act in conjunction with each other in order for medication infusion to occur. In some alternative embodiments a single ASIC may be used, or a single dual processor integrated ASIC may be used. In a single processor device one or more circuits may be provided to monitor the operation of a CPU in the processor to ensure it continues to operate properly in one or more key functions. In the single dual processor integrated ASIC, dual circuitry would be provided so that each processor could act independently of the other. In the single dual processor embodiment, a single off-circuit oscillator may be used to drive both processors or each may have an independent oscillator. A single chain of timing circuits could be used in driving both processors or independent chains of timing circuits could be used. Furthermore, if a single oscillator is used to drive both processors, then one or more separate circuits such as a counter and an RC timer may be used to verify appropriate operation of the oscillator and/or any particular timing circuit dependent thereon.

In different embodiments, more or less of the control electronics may be implemented within one or more processor ICs while any remaining portions may be implemented external to the processor IC(s). The processor IC may be referred to as an MD processor if used in the medical device portion of the system or a CD processor if used in the communication device portion of the system. In other embodiments the process IC used in the communication device may be different, e.g. have a different CPU or different peripheral modules, from a processor IC used in the medical device. In embodiments where more than one processor IC is used in either the medical device or the communication device each of the processors may be different. They may be specifically designed for their intended roles when they perform at least partially different functions.

Depending on particular design constraints portions of the electronics not embodied in the processor ICs may form part of one or more hybrid circuit boards or be otherwise mounted within, on, or even in some cases external to a device housing.

Each processor IC of the present embodiment includes a 16-bit core CPU which is a CMOS low power version of the INTEL 8086 processor and various peripheral modules that are used for system control, data acquisition, and interfacing with electrical components external to the processor IC. The peripheral modules of the processor IC of the present embodiment include (1) a non-volatile memory interface module, e.g. a SEEPROM interface module, (2) a boot ROM module; (3) an SRAM module; (4) a memory decoder module; (5) a crystal oscillator module; (6) a timer module; (7) a pump interface module; (8) a watchdog module; (9) an RF module; (10) an interrupt handler module; (12) an analog-to-digital converter module; (13) an LCD clock driver module; (14) an alarm interface module; and (15) first and second synchronous serial interface modules.

In alternative embodiments fewer, additional, or different peripheral modules may be incorporated into the processor ICs. In one extreme the processor IC may simply incorporate a CPU with all other modules being external thereto. In the other extreme almost all, if not all, electronic components may be incorporated into a single processor IC. Intermediate alternatives might incorporate a single additional module into the processor IC (in addition to the CPU), others might incorporate more than one, e.g. 4 or more, 8 or more, or the like. In still other alternatives, the number of peripheral modules or components in an entire device may be considered and more than a certain percentage of them incorporated into one or more processor ICs, e.g. more than 50%, more than 75%, or even more than 90%.

The processor ICs are responsible for basic system management and communication of information between the implantable device and the external communication device through the RF telemetry link. The telemetry systems of the present embodiment are implemented in part through electrical hardware and in part through software controlled by a processor IC.

In the present embodiment, most of the required electrical modules for the implantable device are integrated within the processor ICs. However, several are not. These additional modules include two independent crystal oscillators (one for each ASIC); two non-volatile memory modules (one for each ASIC), e.g. SEEPROM chips; a volatile memory module (used only by one of the ASICs), e.g. an SRAM chip; pump driver circuitry (partially controlled by the each ASIC); front end telemetry system circuitry; and voltage measurement circuitry associated with the pump driver circuit; a buzzer; and a battery.

Within the implantable device telemetry operations are controlled by a single ASIC (sometimes known as the main processor) The other processor (sometimes known as the monitor processor) controls the buzzer and is thus responsible for audio communications coming from the implantable device. The medical functionality of the implantable device (i.e. the administration of insulin in the present embodiment) is controlled by both processors. To maintain the implantable device in a fail safe operational mode, these two processors maintain an appropriate level of agreement concerning infusion instructions an error condition results and either pumping is halted or a system reset may be made to occur. The main and monitor processors communicate with each other through the use of hardwired serial input and output ports.

As with the implantable device, the control electronics of the external communication device are centered around an ASIC that controls and interacts with a number of peripheral modules. These peripheral modules include an LCD display and driver, an IR port and driver, a crystal oscillator, a keypad and keypad interface, power management modules and reset circuitry, external volatile memory (e.g. SRAM) and non-volatile memory (e.g. SEEPROM), a buzzer, and front end telemetry hardware.

Basic timing for each of the medical device and the communication device is provided by a low power crystal oscillator module within each processor IC that is connected to an external crystal oscillator. In the present embodiment the crystal oscillators are configured to provide a stable clock source of 1,049,100 MHz with a tolerance no greater than +/−500 parts per million (ppm) including drift due to aging, and variation in oscillation due to temperature variations within a range of −10° to 50° C. This frequency and it tolerance are selected such that the lower extreme of the range is still slightly larger than a desired frequency (e.g. 1,048,576).

The clock source is used to drive a 20 bit system clock ripple counter that is sometimes referred to as Counter B (CNT B). This ripple counter is used to provide system clocks of various frequencies for operation of all other modules. Based on the above noted tolerance allowance on the crystal oscillator frequency, drift in the concept of timing between the medical device and the communication device can be as large as about 0.1% or about 3.6 seconds per hour. Though this level of drift may be acceptable for some purposes, it is not acceptable for others. In particular it is not acceptable for maintaining accurate time of day tracking over extended periods of time (e.g. 1 second shift per week) and it is even less acceptable for maintaining a level of time synchronization between the two devices that allows optimized efficiency of telemetry operations (e.g. 1 millisecond every 4 hours).

A pulse stealer circuit is provided for precise system timing of selected clock signals. In the present embodiment the pulse stealer function is applied to the clock signal that has a frequency, as provided by the system clock ripple counter, that is slightly more than an 8192 Hz target frequency. The pulse stealer circuit gives the ability to periodically steal single pulses from a selected clock signal to produce a clock signal of lower average frequency. In the present embodiment the modified signal, or pulse stolen signal, is used as the source for the lower frequency clocks that are also generated by system clock ripple counter. As some lower frequency non-pulse stolen clock signals are desired for various uses in the system they are derived from higher frequency signals that are extracted from the ripple counter above the pulse stolen levels. In implementing pulse stealing for the present embodiment, the CPU loads a 16 bit value into two eight bit configuration registers. The timer whose signal is to be modified is used to cause a counter to count up from zero to the value loaded into the registers. After the counter reaches the value specified in the registers, a single pulse is removed from the output signal (stolen from the output signal) to provide a modified output signal. Then the counting begins again from zero and the process is repeated over and over so that a modified output signal, or pulse train, having a desired average frequency is generated.

A value of 0x0000 loaded into these registers disables the pulse stealer and allows the approximately 8,192 Hz clock to pass though unmodified (i.e. input signal=output signal).

Figure 4A:
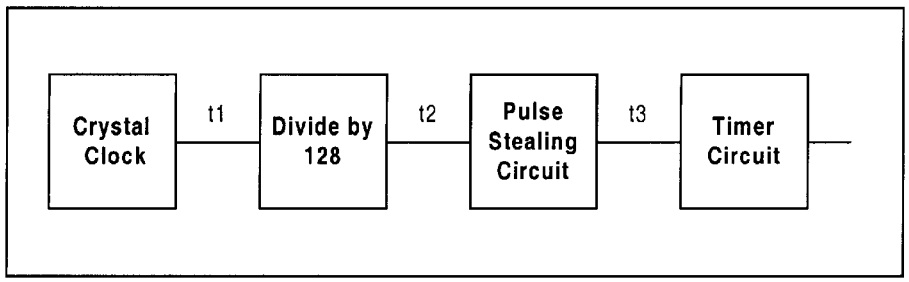
FIG. 4a depicts a block diagram of components that may be used in a pulse stealing device as is used by both the implantable device and the external communication device of the first preferred embodiment.

FIG. 4a, presents a block diagram showing the primary elements of a pulse stealing circuit: (1) a crystal clock 242, (2) a divide circuit 244, (3) a pulse stealing circuit 246, and (4) a timer circuit 248.

In the present embodiment the crystal clock 242 operates at a nominal frequency of 1,049,100 Hz +/−500 Hz producing pulse train identified as "t1". The divide circuit 244 in the present embodiment effectively divides by input frequency by a value X that is 128 and produces pulse train "t2" of nominal frequency 8196 Hz +/−3.9 Hz. The pulse stealing circuit removes a single clock pulse repetitively from t2 to produce t3. The repetition rate is controlled by a programmed value set in the pulse stealing circuit. The repetition rate is set to an appropriate value that adjusts the input frequency (t2) to that desired by the timer circuit 248. In the present embodiment, it is desired that the pulse train t3 that feeds timer circuit 248 be precisely operating at 8192 pulses/second.

The pulse stealing circuit includes a counter that runs off clock signal t2. The counter begins counting at zero and counts up to a value set in the above noted configuration registers. When the counter reaches the programmed value, one clock pulse is removed from the signal t2 to produce signal t3. The counter is reset to start the count again and continues in an endless loop.

Figure 4B:
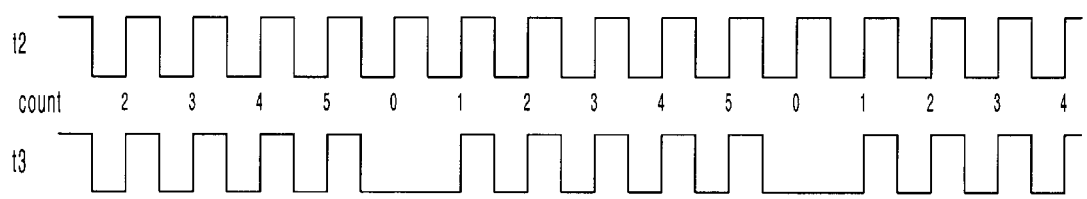
FIG. 4b depicts an example of the differences between a pulse stolen chain and a non-pulse stolen chain.

FIG. 4b depicts a sample timing sequence for the input signal t2 and output signal t3 of the pulse stealing circuit where the register value is set to five.

The timer circuit produces a pulse stream t3 having an effective average clock frequency of, $$\left(1 - \frac{1}{\text{Value} + 1}\right) * (\text{Frequency of } t2),$$

where "value" is the value entered into the configuration registers.

The table presented below illustrates the effect of the pulse stealing register value on the timer circuit clock.

| Pulse Stealing Impact | |
| --- | --- |
| Value in the Configuration Registers | Timer Circuit Clock Frequency (t3) Relative to Input Frequency (t2) |
| 1 | ½ |
| 2 | ⅔ |
| 3 | ¾ |
| 4 | ⅘ |
| 5 | ⅚ |

In the present embodiment, the pulse stealing circuit is designed to achieve an effective average timer circuit clock frequency of 8192 Hz. The required pulse stealing register value may be calculated from, $$DF = \left(1 - \frac{1}{\text{Value} + 1}\right) * (\text{crystal frequency})/X,$$

where DF is the desired frequency, and in the present embodiment is 8192 Hz, and where X is the amount by which the crystal frequency is divided prior to entering the pulse stealer, and in the present embodiment is 128. This equation may be manipulated to yield, $$\text{value} = \frac{\text{crystal frequency}}{\text{crystal frequency} - 1048576} - 1,$$

where the value used for X was 128.

The table below illustrates some example register values based on example crystal frequency values.

Sample Register Values Table

| Crystal Frequency Hz | Register Value |
| --- | --- |
| 1,048,576 | Cannot calculate = 0 |
| 1,048,700 | 8456 |
| 1,048,900 | 3236 |
| 1,049,100 | 2001 |
| 1,049,300 | 1448 |
| 1,049,500 | 1134 |
| 1,049,624 | 1000 |

If, for example, the crystal frequency was measured to be 1,049,039 Hz. The calculated register value is 2264.74. However, since in the present embodiment the counter only accommodates integer register values, the register value will be set to either 2265 or possibly 2264. As a result, by use of this register value, the average frequency of signal t3 will be brought as close as possible to the desired value.

A sample pulse stealing circuit for the present embodiment that uses up to a 16 bit pulse stealing value might include a 16 bit register, a 16 bit counter, a 16 bit compare logic block, and a logic gate such as an "and" gate that takes two inputs, t2 and a normally high signal that is toggled low when the counter reaches the register value and then is reasserted high when the counting starts over. The compare logic block may be used to compare the value in the register to the value in the counter to determine if the two are equivalent. The compare logic block may be based, for example, on 16 two-input AND gates whose outputs are fed into one or more additional AND gates to produce a single output signal indicative of whether the count has been met. As required, additional logic could be added as necessary, to interpret a 0000 h register value as disabling the pulse stealer.

Of course, in other embodiments the pulse stealing circuit may be driven by a different signal t2 frequency or it may be driven directly from the crystal clock. It may be made to steal more than one consecutive pulse. A different register size may be used. The signals generated by the pulse stealer may be used either directly by a circuit that is tolerant to a missing pulse or it may alternatively be used to drive one or more additional counters, or "divide by" circuits, wherein with each subsequent reduction in frequency, the uniformity of the final pulse train is improved as well as any difference between the modified frequency and the desired frequency.

In other alternative embodiments, pulse stealing circuits may be independently used on multiple modules or they may be stacked in series to provide an even more accurate average signal pulse frequency. The register value may be set once and then let alone or alternatively, it may be changed periodically based on a defined criteria. For example, if a given crystal oscillator circuit is known to vary its oscillation frequency with temperature, or other parameter, the parameter may be measured and a revised value determined. The revised value may be determined by use of a look up table, calculation, or the like and then inserted into the register or otherwise used to institute pulse stealing.

As another example, if an increment in time as registered by a second clock were compared to the same increment of time as measured by a first clock, a drift rate or amount could be derived. The drift rate or amount could then be used to calculate a revised pulse stealing value or additional pulse stealing value for one or both of the clocks so as to more closely synchronize their operation.

As further example, if the count value entered in the registers is not precisely the desired value, the value entered into the register may be periodically varied so that the average value in the register is closer to the desired value. As such, in one implementation the values entered into the register may alternate between the two values that bound each side of the desired value. The proportion of the time that each of the bounding values is used may be based on the proportions of the differences between the desired value and each of the two bounding values. The period of time over which each value is used prior to switching to the other value may vary depending on the amount of error that is allowed to build up. For example, the period may be smaller than one minute or larger than one day. In other alternatives, other implementations are possible, for example where one of the alternative values used is something other than an immediately bounding value.

In the present embodiment telemetry reception and transmission timing by both the medical device and the communication device are based on time periods that are derived from the pulse stolen clock signals. As these pulse stolen clock signals have truer frequencies (on average) than do the signals generated by the principle oscillator, the telemetry timing between the two devices will stay better synchronized. Furthermore as the incrementing of the time of day clock in the communication device is also is derived from the pulse stolen oscillator signals, the time of day clock remains better synchronized to the actual time than it otherwise would have been. The pulse stolen clock signals are not used for driving circuits or functions that cannot tolerate missing pulses, e.g. pulse trains that are transmitting telemetry data.

The telemetry system for the implantable device and the external communication device provide a half-duplex link between each other using a carrier frequency of about 250 kHz (e.g. about 2^18 Hz) and a data signal having a frequency of about 8 kHz (e.g. about 2^13). The transmitter hardware uses an 8 kHz data signal to modulate the carrier signal to generate signals that will be transmitted by the antenna. The receiver hardware receives the modulated signal and demodulates it to extract the 8 kHz data signal. Both the implantable device and the external communication device have transmit and receive capabilities to allow two-way communication.

Most of the RF telemetry circuits necessary for communication between the external communication device and the implantable device are implemented in the processor IC. In order to minimize the digital noise interference that the processor IC might impart to the weak RF signals that are being received, a high-gain RF amplifier is implemented off-chip. Also an RF antenna, that is used for both transmission and reception, and circuitry to select between reception and transmission are implemented off-chip. The remaining analog sections and all the digital demodulation circuits are implemented in the processor IC.

The RF module of the processor IC outputs in phase and quadrature phase signal components for combined transmission by the external antenna. The RF module also supplies a control signal that is used to switch between a transmission configuration and a reception configuration. The RF module receives as inputs signals from the amplification circuitry.

A Quadrature Fast Acquisition Spread Spectrum Technique (QFAST®) is used as the modulation technique. QFAST® modulation is based on an Offset Quadrature Phase Shift Keying (QPSK) modulation technique. In this technique, data generated by the CPU modulates clock signals at the carrier frequency. As a result of quadrature modulation, in-phase and quadrature-phase components of the given data stream are generated. The two components are then applied to opposite ends of the external antenna so that a combined signal is transmitted.

The transmitter section of the telemetry system receives byte wide parallel data packets from the CPU and then loads the data into a parallel-to-serial shift register. The serial data is then sent to the QFAST® RF modulation transmitter section to modulate two quadrature clock signal components each operating with a carrier frequency of about $2^{18}$ Hz) and shifted in phase relative to each other by 90 degrees. The two components are then delivered to opposite ends of the antenna. As long as there is data in the transmitter parallel-to-serial shift register, the RF transmitter remains activated. If the transmitter doesn't have data available when the next byte is to be transmitted the message is considered to have been completely transmitted and the CPU shuts off the transmitter circuitry so as to minimize continued power drain.

As noted above, external to the processor IC, the received RF signal is amplified by a high gain receive amplifier. A bandpass filter is used to attenuate out-of-band components such as those due to AM radio stations. The amplified RF signal then enters a mixer in the RF module of the processor IC and is converted to baseband using two mixers, one in-phase mixer and one quadrature phase mixer both at the carrier frequency. The mixer outputs are the quadrature components of the baseband signals. An integrator & dump function in the RF module then removes the sum frequency (2 fc) and high frequency noise (i.e. acting as a low pass filter) from each of the two signals. The processed signals are then digitized using a comparator and passed to the demodulator where the data and clock are recovered.

In QFAST®, data rate adaptability is accomplished through a spread-spectrum "coding gain" concept, with the spreading code being a simple clock. The modulation produced by the QFAST® modulator is demodulated in a manner which delivers both clock and data. All of the QFAST® modulation and demodulation circuits are digital and are incorporated into the processor IC.

The QFAST® technique provides a communication system with a number of attributes: (1) it extracts the clock from the received signal without a clock recovery loop; (2) it provides demodulation of data without phase ambiguity and without the requirement for synchronous demodulation; (3) it makes effective use of the available transmission bandwidth, (4) it results in fast acquisition of the message signal; (5) it is relatively immune to the effects of highly dispersive and distorting propagation media; (6) it does not require regeneration of a phase-coherent local replica at the receiver of the transmitted carrier; (7) it does not require resolution of ambiguity between the in-phase and quadrature-phase channels in the receiver; and (8) it does not exhibit data phase ambiguity.

Further detail about QFAST® (Quadrature Fast Acquisition Spread Spectrum Technique) may be found in U.S. Pat. No. 5,559,828, entitled Transmitted Reference Spread Spectrum Communication Using a Single Carrier with Two Mutually Orthogonal Modulated Basis Vectors, by Armstrong, et al.

The RF module in the processor IC consists of timing circuitry, circuitry to maintain time synchronization between the implantable device and the external communication device, a digital RF transmitter section that includes a QFAST® RF modulation transmitter, an analog receive module, and a digital receive section that includes a QFAST® RF modulation receiver.

The RF communication between the implantable device and the external communication device occurs in the form of messages (sometimes referred to as communication signals or packets) that are passed back and forth between the two devices. In this embodiment these messages have a multipart format or protocol: (1) preamble, (2) frame sync, (3) telemetry identifier, and (4) data.

In other embodiments other multipart formats may be used. For example, the multipart format might consist of (1) a preamble, (2) a telemetry identifier, and (3) data. In still other embodiments the preamble and frame sync may be combined into a single entity, or the telemetry identifier and the frame sync may be combined into a single entity, or even all of the preamble, frame sync, and telemetry identifier may be combined into a single entity such that the functionality of associated with these individual elements of the messages of the present embodiment may be performed simultaneously or in series based on a single but repeated pattern of information.

For communications from the implantable device to the external communication device the preamble is a repeating pattern of "10", i.e. 10101010. This alternating pattern of ones and zeros is broadcast for 8-bit times. This pattern is considered the standard preamble pattern. In other embodiments this standard preamble pattern may be different from that noted above (e.g. it may be a repeated pattern of "01" instead of "10"). Though, unnecessary, the standard preamble need not transition with every other bit though, as a certain number of bit transitions are typically necessary to establish bit synchronization, the more transitions, the shorter the minimum length that the preamble can take.

For communications from the external communication device to the implantable device, the preamble is either of the standard preamble pattern but applied for an extended number of bit times (e.g. 24, 48, or 96) or is of an attention preamble pattern that is applied for, typically, even a longer extended number of bit times. In other embodiments, not only may the preamble used by the implantable device and the external communication device have different lengths as used in this embodiment, they may also use different standard preamble bit patterns. Of course in still other embodiments, a same preamble length may be used by both the implantable device and the external communication device whether or not the same standard preamble bit pattern is used. The attention preamble pattern is formed of a repeated pattern of "110110 . . . 110". In other embodiments, other attention preamble patterns may be used (e.g. repetitions of "011", "100", "001", "1011", and the like).

The preamble, whether of the standard pattern or the attention pattern, is used so that the RF reception hardware can establish bit synchronization (i.e. bit boundary recognition) of the incoming data. However, the attention preamble is further used to get and hold the receiver's attention for a defined period of time. As long as the attention preamble is being received, the receiver's hardware will stay on and continue tracking the signal in anticipation of an incoming message. In other embodiments, the concept of a standard preamble pattern that will not hold the receiver's attention may be dispensed with in favor of always using a preamble that is in effect an attention preamble.

The attention preamble is considered to be lost, or no longer being received, when the receiver receives more than 2 inappropriate bit values during receipt of any 64-bits or when the frame sync pattern is received.

Before beginning error detection, the receiver's hardware first requires that the receipt of the attention preamble be established. In establishing receipt of the attention preamble the receiver's hardware may load the received bits into a shift register and may then compare the shifting pattern to a predefined pattern of selected length and then may consider the receipt of the attention preamble to be established once the comparison indicates a match of sufficient length has occurred The receive hardware then continues to compare received bits to predicted bits based on the pattern established. A bit counter is incremented with each bit received and an error counter is incremented with each error detected. The bit counter is reset whenever an error is detected. The error counter is reset whenever the bit counter reach a preset value. If the error counter should reach a predefined error amount, the established attention preamble is considered to have been lost and if the receiver is still operating within its listening period, the receiver's hardware continues its process of trying to establish receipt of attention preamble. The parameters associated with establishing receipt of the attention preamble and associated with the setting of error tolerances may be hardcoded into the system or they may be programmable into hardware registers.

It is preferred that the above analysis be implemented in hardware due to the energy saving possible but in other embodiments the process may be implemented via software.

Of course in other embodiments, the error tolerance believed acceptable may be increased or decreased or defined in a different manner. For example, instead of using an error tolerance of 2-bits out of 64-bits, one might use a tolerance of $1/32$. The tolerance may even be increased to $2/32$, $3/64$, $4/64$, or even higher. Alternatively, it may be decreased to $1/64$, $1/128$ or even to zero.

The attention preamble may be used when there is some uncertainty in the time synchronization of the two devices. The extra length of the attention preamble allows the receiver's reception window to open a little latter than anticipated and to still have the receiver pick up the entire message. The extra length of the attention preamble allows the receiver's reception window to open earlier than anticipated, so long as a minimum number of bits are heard by the receiver during the time its reception window is normally open, and still have the receiver's attention locked onto the preamble and have the receiver remain on as long as the attention preamble is being received, plus a little more, in anticipation of receiving a frame sync pattern.

The receiver may miss some of the initial bits in the preamble but a minimum number of bit transitions (e.g. 4, 6, or 8 transitions) of the preamble pattern must be received to ensure bit synchronization between the transmitted message and the receiver. In the present embodiment, the implantable device broadcasts with a minimal preamble size in order to reduce power consumption within the implantable device. In other embodiments, the preamble used by the implantable device may be larger relative to the minimum number of bit transitions needed to establish bit synchronization.

In the present embodiment, frame sync may actually be considered byte sync (i.e. frames are bytes) and is a single byte of a selected pattern and is used so the receiver can obtain byte boundaries for the transmitted data. In the present embodiment, the selected pattern is "10110000". In other embodiments, other patterns, pattern lengths, and frame sizes may also be acceptable for use as frame sync so long as the patterns (in combination with preamble or attention preamble patterns and any tolerances in their reception) cannot lead to errors in defining byte transitions. In still other embodiments, the attention preamble pattern may be of the same bit pattern as the frame sync, in which case, some error tolerance may be allowed in the frame sync pattern and the receiver's attention would be held until the pattern is lost or a valid telemetry ID pattern is received.

Even during the receipt of attention preamble (or other preamble) the receiver continually compares shifting bits that are received to the anticipated frame sync pattern. The Frame Sync byte may be detected by feeding the incoming bit stream into a shift register and passing the bit values in the register to the inputs of an 8 input AND gate whose input assertion levels correspond to the anticipated frame sync pattern.

This comparison process continues so long as the receiver continues to listen for an incoming message or until a valid frame sync pattern has been received. If the receiver is continuing to listen beyond its normal reception window (i.e. listening period), due to the reception of an attention preamble, the listening will not stop immediately upon the attention preamble being lost. The comparison process for ascertaining the receipt of frame sync continues for a number of bits after attention preamble is lost, even if the listening period has ended, as its loss may be associated with the partial receipt of frame sync. Once frame sync is received a valid frame sync signal is asserted.

In the present embodiment, the telemetry identifier (i.e. telemetry ID) is a 3-byte value that is used to ensure that only the intended receiver receives a message. The value of all "1s" indicates a universal message that is to be received by all receivers, otherwise the telemetry ID must be agreed upon between the receiver and transmitter. A unique ID is provided for each implantable device and each external communication device during manufacturing. Only the external communication device can transmit a message using the universal ID code. The telemetry IDs that the receiver will consider to be valid are the ID of the receiver or the universal ID. All other incoming bit patterns will be rejected with the result that the receiver will be either turned off or will start again looking for a valid frame sync pattern attention preamble. In alternative embodiments, instead of the receiver accepting only its own ID (in addition to the universal ID) it may instead accept the ID of the transmitter. In other alternative embodiments, a different length preamble may be used by the implantable device and the external communication device. In still further alternatives, the telemetry IDs may not be unique if it is believed that the chance of miscommunication between devices is not a significant risk. In fact, if there is little risk of miscommunication, telemetry ID may be dropped from the message protocol.

Other embodiments may retain the concept of telemetry ID for either the receiver or the transmitter or both but only pass the telemetry ID information implicitly. Such implicit transfer might use the telemetry ID information in generating a validation code (e.g. CRC) that is transferred with the message. In such cases the receiver could compare the received code to one or more different codes generated using each of the unique telemetry ID and the universal telemetry ID. These embodiments would be less preferred when power consumption considerations are critical, as the telemetry system of the receiver would have to remain on to receive the entire message in order to determine whether the message was for it or not.

After a Frame Sync byte is detected, the processor IC hardware compares the next 24 bits of the incoming data to the personal ID bits and to the universal ID which in this embodiment is fixed at 0xFFFFFF. The detection for the universal ID may be performed by passing the incoming data stream (for these 24 bits) through an XOR gate along with another input fixed at a value of 1. The output of the XOR gate may then be fed into the data line of a D flip-flop while the clock line of the flip-flop is fed by a clock signal running at the bit rate. If the 24 bits are processed without the output of flip-flop changing state a valid universal ID has been received. If the flip-flop does change state, a universal failure signal is asserted. The incoming bits are also passed through a first input of a second XOR gate while a second input of the gate is supplied by a multiplexer that provides bit values from the specific acceptable telemetry ID. The output of the XOR gate is provided to a flip-flop in a manner analogous to that discussed above for detecting the universal ID. So long as the output of the flip-flop doesn't change state during the processing of the 24 bits, a valid specific ID is considered to have been received, otherwise a specific ID failure signal is generated. If and only if one of the ID failures is asserted, an ID valid signal is generated. If both ID failures are generated, the valid frame sync flag is de-asserted in which case listening by the receiver may be aborted if the listening period has expired or listening for attention preamble and frame sync may continue if the listening period has not yet expired. If a valid telemetry ID is received, the receiver listens to the remaining portion of the message.

In alternative embodiments the frame sync and telemetry ID may be combined into a single entity that is identified as a whole as opposed to the present embodiment where the two pieces are looked for and identified separately.

In the present embodiment, data is provided in an integer number of bytes following the telemetry ID. In the present embodiment the first byte of the data indicates the message type. The first seven bits of the first byte is an operation code or op-code while the eighth bit is either ignored or is set and interpreted as a sequence number (to be discussed hereafter) dependent on whether or not the first seven bits call for a sequence number or not. Each op-code, based on its nature, is followed by data in a defined number of bytes. The specific op-code itself may dictate the number of bytes that follow or alternatively the specific op-code may dictate that the number of bytes to follow may be extracted from the first byte or several bytes of information that follow it. In alternative embodiments, op-codes may have a different length, or not be used at all, the message length or message end may be dictated in other ways. Based on the op-code and potentially one or more bytes following it, the receiver knows exactly how many more bytes of data to listen for. After receiving those bytes, the receiver may be turned off to conserve power.

For some messages dealing with drug delivery, the data portion of the message may include a bolus number. The bolus number is similar to the sequence number in that it is incremented by both the implantable device and external communication device under controlled conditions so as to reduce the possibility of bolus requests being delivered more than once when duplicate requests may be made as a result of the external communication device failing to receive a confirmation that a previous request was received. The bolus number may be a single bit number in some embodiments but in more preferred embodiments it is a multibit number (e.g. 2-bit, 4-bit, 7-bit, 1-byte, or 2-bytes) so that it can take on more than two values thereby making it less likely that an error will escape detection due to received and expected numbers erroneously matching. The incrementing of the bolus number may occur within the external communication device when it receives confirmation that a message was correctly received and it may be incremented by the implantable device when it correctly receives a bolus request. As such when a duplicate request for a bolus is received by the implantable device it can recognize that the expected and received bolus numbers do not match and that requested bolus is not a new request. As such the implantable device can respond to the repeated request that the bolus was correctly received and delivered (with out performing a second delivery and without incrementing its expectation of what the next bolus number will be).

In other embodiments, other incrementing numbers may be used to help ensure that only appropriate operation of the implantable device occurs. For example, incrementing temporary basal rate numbers may be used, and/or separate incrementing numbers may be used for different types of boluses that might be requested, e.g. immediate boluses and temporary boluses. In still further alternatives, incrementing message numbers may be generally used. These message numbers may for example be used on all messages that have responses associated therewith. Once the receiver confirms that a message was appropriately received it may increment its message number. Similarly, once the transmitter gets a response to the message it sent, it may likewise increment its message number.

In the present embodiment, the data portion of the message ends with a one or 2-byte validation or error checking code (its type is dictated by the op-code included with the message). The preferred error checking code of this embodiment is in the form of a cyclic redundancy code (CRC). In other embodiments, the CRC may be replaced with another error checking code and/or it may be placed in a different part of the message or even deleted from the message protocol completely. The op-code may also be placed in another part of the message, or deleted in favor of other techniques that may be used in interpreting the message and for determining when the end of the message has been properly received.

In the present embodiment it is preferred that the CRC occur at the end of the message as it simplifies the computational efficiency of confirming the validity of the message by the receiver. In alternative embodiments, where message compilation and transmission occur in parallel, placing the CRC at the end of the message also allows the data to be processed and transmitted in a single pass without a need to have storage space for the entire message available.

In order to keep power requirements low in a preferred implementation, the external communication device and implantable device attempt to maintain a common time base, transmissions are set to start at specified times, and reception windows are set for specified times and lengths. In this way, the receiver may remain in a powered down mode most of the time and can turn on to listen for a potential incoming message at the specified times for the specified lengths of time. If a message is found to be incoming, the receiver stays on, otherwise it goes back to sleep (i.e. power down mode).

In the present application, to avoid ambiguities in some portions of the description relating to the timing associated with the transmission and reception of messages, the following definitions will be used: (1) "inbound" will generally refer to activities associated with telemetry reception by the medical device, whether implanted or not, or to activities associated with telemetry transmission by the communication device, (2) "outbound" will generally refer to activities associated with the telemetry transmission by the medical device, whether implanted or not, or to activities associated with telemetry reception by the communication device.

According to a telemetry timer in the medical device, outbound transmissions begin at an "outbound transmission start time" and continue for an "outbound transmission period" which defines the period that the preamble portion of the message is sent which may be though of in terms of time or in terms of the number of data bits. Similarly, according to a telemetry timer in the communication device, inbound transmissions begin at an "inbound transmission start time" and continue for an "inbound transmission period" which defines the period that the preamble portion of the message is sent which may be thought of in terms of time or in terms of the number of data bits.

Furthermore, according to the telemetry timer in the medical device, the telemetry reception system of the medical device begins listening for messages at an "inbound listening start time" and continues to listen for an "inbound listening period" which may be thought of in terms of a time period or a given number of data bits. Similarly, according to the to the telemetry timer in the communication device, the telemetry reception system of the communication device begins listening for messages at an "outbound listening start time" and continues to listen for an "outbound listening period" which may be thought of in terms of a time period or a given number of data bits. Additionally an "inbound listening interval" may be thought of as the interval between the successive inbound listening start times while an "outbound listening interval" may be thought of as the interval between the successive outbound listening start times. Throughout the specification, the above timing elements may be referred to in different ways particularly when it is believed that the intended meaning is clear from the context of the description. However, when the precise meaning is required, descriptions will be based on the above definitions so as to remove ambiguity.

In the present embodiment time synchronization for telemetry communication is maintained using two techniques. The first technique periodically determines the present difference in the concept of time (e.g. second boundaries) as held by the communication device and medical device and the difference is used to reestablish synchronization of the timers. In the present embodiment, reestablishment occurs on the part of the communication device each time it receives a valid communication from the medical device.

The second technique determines a rate of drift that has occurred between the concept of time held by the communication device and that of the medical device. The determined rate of drift is used in combination with a determined lapse in time to estimate how much drift has occurred. This amount of drift is then used in shifting a listening start time or transmission start time of a first one of the devices to match what is believed to be the potential transmission period or listening period of a second one of the devices. In the present embodiment, the first device is the communication device, though in other embodiments it could be the medical device.

In alternative embodiments, variations in drift amounts may be used to extend listening periods and/or transmission periods. They may also be used to force the start of listening or transmission to lead the best estimate of the transmission or listening start times that that the other device is using. For example, the start of listening or transmission may be pulled forward by about one-half the amount of extension applied to the listening or transmission periods, respectively, Timer periods indicative of reception start times (i.e. listening times) may be generated using a clock signal (i.e. RF one second clock signal in the present embodiment) that is based on a pulse stolen signal (e.g. $2^{10}$ Hz signal generated by the system clock ripple counter in the present embodiment) plus or minus a value stored in an adjustment register (i.e. REG B in the present embodiment which is discussed hereafter). The beginning of a reception period is determined by passing the RF one-second signal through a start counter and comparing the value of the start counter to a predefined value stored in a start register using a first comparator. The value in the start register dictates how often reception will automatically be enabled relative to the clock signal that drives the first counter.

In the implantable device of the present embodiment a programmable but fixed value of 0×1000 is set into REG B which implies an adjustment of zero to the RF one second clock signal (as will be discussed hereafter). Also in the implantable device of the present embodiment, the value set in the start register is a programmable amount that is set at two for normal operations and as it is driven by a 1 Hz clock signal, reception is started every 2 seconds. In the communication device of the present embodiment, the value used in REG B is varied and the value set in the start register in combination with the REG B value sets the interval between listening start times to nominally 60 seconds.

When the register value and counter value match, a signal may be generated by the first comparator to initiate reception. The output signal may also be used to clear and enable a period counter that is incremented based on a signal of desired frequency (e.g. about a 8,192 Hz signal). The value in the period counter is compared to that in a period register using a second comparator. When the values are equal, the second comparator outputs a period signal that resets the value in the first counter and resets the value in the second counter. The period signal may be used to end reception. The resetting of the value in the first counter prepares it for the use in establishing the start of next listening period. This control technique works because the listening period defined the second counter and second comparator is less than the duration between successive counts of the first counter. In the present embodiment as the duration is set by a single 8 bit register and the clock driving the counter matches the bit rate for data reception and transmission, the maximum duration is 256 bit times (e.g. $\frac{1}{32}$ of a second when using an 8 kHz bit rate). In other embodiments, clock signals other than that corresponding to bit times may be used.

The value placed in the listening period register in combination with the frequency of the counting dictates the time period between the start listening and end listening times. The start signal and period signal may be used in controlling the autonomous listening behavior of receiver. In an alternative embodiment, the period signal may be not be used to immediately shut down the receiver but instead an additional period of time may be allotted (e.g. 1 mS) before shut down so as to allow the system to once again check to see if an entire frame sync pattern has been received. This enhancement avoids shutting down the receiver when a message may have been incoming but in an intermediate state of having attention preamble already ended but frame sync not fully received at the time the period signal was issued.

In the present embodiment, the time boundaries critical for RF transmission and reception are the second boundaries and the minute boundaries. In optimizing the ability of the system to operate at low power, the external communication device and the implantable device are caused to maintain time synchronization. In the present embodiment, dedicated hardware is used to provide enhanced synchronization. In other embodiments a similar enhancement may be provided in part by software though at a probable increase in power consumption.

In the present embodiment, timer inaccuracy is observed as a difference between the timing signals generated in the pulse stolen 8192 Hz clocks (time of day clocks) in the external communication device and the implantable device. However, if the pulse stolen clocks are running at slightly different frequencies the time-of-day values in the two units will slowly diverge. These difference may result from, for example, fluctuation in the oscillation frequency of the crystal oscillator due to temperature fluctuation or due to slight inaccuracies in the pulse stealing values used. As noted above, the purpose of the time synchronization operations of the present embodiment are to (1) periodically set the time of day timers in the two devices to the same value, and (2) compensate for relative drift between the two timers between resettings.

In order to achieve synchronization, the implantable device is considered the master and the external communication device synchronizes its time-of-day counter periodically with the time-of-day counter in the implantable device. In the present embodiment, synchronization is performed every time a valid message is received from the implantable device. As a correction factor, by definition, is not needed in the implantable device, the RF time synchronization function is disabled by software in the implantable device for both the main and monitor processors. In other embodiments, the implantable device instead of the communication device may perform the time synchronization function. In still other embodiments, a modified version of the time synchronization technique may be used to maintain synchronization between the two processor ICs in the implantable device.

Time Synchronization is used to minimize power consumption on the implantable device side of the system. the external communication device uses the following hardware to keep track of the passage of time and can transmit telemetry data bound for the implantable device within the listening periods used by the implantable device.

Figure 5:
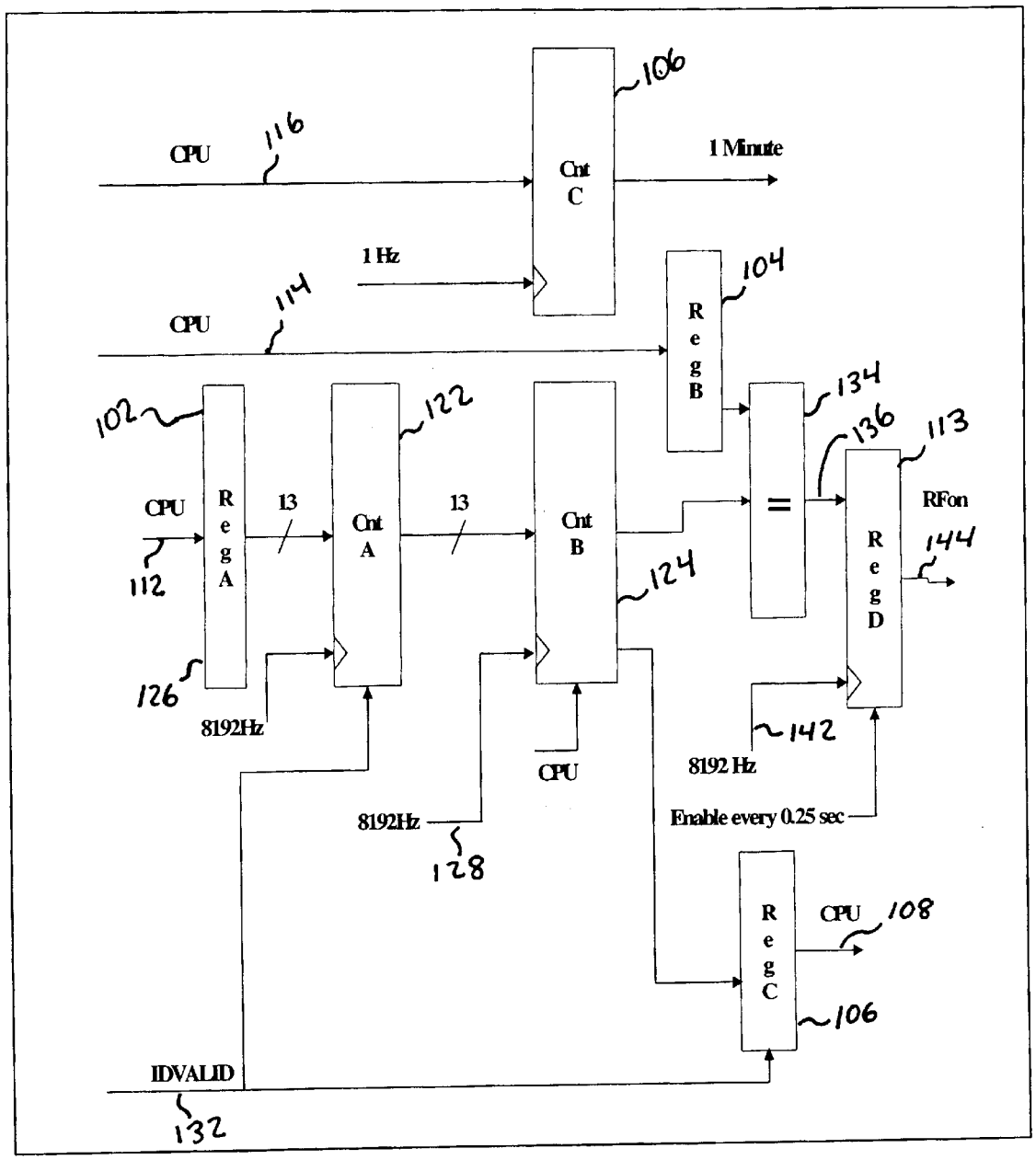
FIG. 5 depicts a block diagram of a time synchronization module that is used in the first preferred embodiment.

FIG. 5 illustrates a block diagram of the various hardware components and signals used for time synchronization. Register A (REG A) 102, Register B (REG B) 104, and the Counter C (CNT C) 106 are loadable by the CPU as illustrated by lines 112, 114, and 116, respectively. Counters A (CNT A) 122 and Counter B (CNT B) 124 both have the same time base of 8192 Hz as indicated by lines 126 and 128, respectively.

A valid ID signal (IDVALID) 132 is generated when a message for the communication is recognized by the hardware. The IDVALID signal 132 indicates that the hardware recognized the frame synchronization byte and a 24 bit telemetry ID. As soon as IDVALID is asserted, the value in REG A is loaded into CNT A and CNT A continues to count at the same rate as Counter B but with a predefined starting value, i.e. the value inserted from REG A.

The value loaded into REG A by the CPU is known. It represents the number of bit times that have occurred between the beginning of message transmission and the receipt of the telemetry ID. In the present embodiment, it takes a transmission of 40 bits for the communication device to recognize a valid telemetry ID: (1) 8 bits for the preamble, (2) 8 bits for the frame synchronization byte, and (3) 24 bits for the telemetry ID. Altogether it takes 40 bits to have the IDVALID signal asserted. The value loaded into REG A is 40*8192/(incoming data rate). For example, if the data rate is 8192 bits/sec, then the value 40 is loaded into REG A and then loaded into CNT A after IDVALID is asserted. Since the implantable device always starts transmitting exactly on the one second boundary based on its own concept of time, i.e. its B counter value is equal to zero, the IDVALID signal is asserted when the implantable device's B counter is equal to 40. As such the value loaded into CNT A of the communication device is initially 40 but then continues to increase since CNT A continues counting. After the entire message is received, if the CPU determines if the message was valid. If valid, then the value in CNT A of the external communication device is loaded into the CNT B of the external communication device and the implantable device and external communication device are synchronized with respect to time.

In alternative embodiments, the medical device could start its transmission at other than second boundaries and the communication device could still achieve synchronization if the start time information were transmitted with the message so that it could be used by the communication device when performing its analysis. In the present embodiment, the resolution with which synchronization is maintained correlates to the bit rate that is used in data transfer and as such synchronization between the two devices is targeted to be maintained within about 1 bit time. In other embodiments, targeted synchronization resolution may be different from bit time, i.e. it may be greater or smaller. If smaller, corresponding variations in listening periods and/or transmission periods may be necessary to accommodate the potential variance between the timing of the two devices. In still other alternatives, responsibility for maintaining synchronization could be handled by the medical device or by both devices.

Whenever a valid ID (IDVALID) is recognized by the external communication device the value in CNT B is loaded into the Register C (REG C) 106. The value in REG C may be sent to the CPU as illustrated by line 108. This, along with other information, can then be used to determine the relative clock error between the implantable device and the external communication device. The value loaded into REG C minus the value in REG A yields the time difference in bit times between the implantable device's concept of time and the external communication device's concept of time. If the difference is positive, the external communication device's clock is running ahead of the implantable device's clock. If the difference is negative, then the external communication device's clock is running behind the implantable device's clock. Again, using the example above, if the value loaded into REG C is 64, and since we know it should have ideally been 40, we know that the external communication device has gained 24 counts. This gain in counts has occurred since the last time the implantable device's B counter and the external communication device's CNT B were synchronized. Taking into account the time interval since the last synchronization occurred, the error in terms of a rate can be calculated. If the last synchronization occurred 5 minutes ago, the external communication device is running 24 counts per 5 minutes, or about 10 parts per million, too fast. In order to avoid inaccuracies in computing the relative error, each new relative error is preferably, but not necessarily, averaged with the previously computed error. Also, if the time since the last synchronization is too short (e.g. less than 1 to 5 minutes), the error may not be re-computed as it may lack sufficient accuracy. When the drift rate is calculated, it may be used to compute a modified time to start listening for an outbound message (i.e. outbound from the implantable device) or to start transmitting an inbound message (i.e. inbound to the implantable device) based on how much time has lapsed since the last communication.

When the external communication device must communicate with the implantable device, REG B can be used to set a time offset (based on an estimate of drift) to more accurately synchronize the transmission/reception of the message. An estimated drift value may be loaded into register B. This estimated drift value may be derived, at least in part, based on the difference between the value stored in register C and the value stored in register A along with a time difference between the last two synchronizations (e.g. the last two communications), and a time difference between the last synchronization (e.g. the last communication) and the present time.

For example, the estimated drift (ED) may be derived from, $$ED = \frac{Reg\ C - Reg\ A}{Time1 - Time2} * (Time0 - Time1)$$

where Reg A and Reg C are the respective values in Reg A and Reg C, and Time 2, Time 1, and Time 0 are the time of the second to last communication, time of the last communication, and the present time, respectively. A positive value of ED indicates that the external communication device's sense of timing is leading that of the implantable device while a negative value indicates that the external communication device's sense of time is trailing that of the implantable device.

Other ways of deriving the estimated drift value may alternatively be used. As mentioned above, the drift may be determined based on an average of a presently determined error rate and one or more previously determined rates. This type of averaging may be unweighted or weighted, based for example on the relative times between successive measurements. In another alternative, the estimate of drift may completely ignore one or more of the most recent communications and instead be based on the present time and the time of an older communication.

Compare circuit 134 compares a value loaded into REG B with the current value in CNT B. When the values match, the compare circuit sends an output signal 136 to Register D (REG D) 138 which may be a one-shot flip-flop that produces a single output pulse having a width equal to that of one cycle (e.g. about ⅛192 seconds) of the input clock signal 142. The output 144 of Register D may be the RF one second signal that triggers the onset of various telemetry related activities.

In the present embodiment, it is desired that an upper limit on acceptable estimated drift be set, after which the drift will be considered to be excessive and a more extreme technique may be used to reestablish communication. In the present embodiment, if the value loaded into REG D is within a preset tolerance, or drift limit, (e.g. +/−0.25 seconds) of a nominal transmission or receive time (e.g. a 1 second boundary as indicated by CNT B) an RF one second signal is to be generated. Confirmation that the value in Register D is within the preset tolerance may be obtained by comparing selected bit values in Register D to predetermined values for those bits. For example, a bit value of "0001 0000 0000 0000" may represent a one second boundary in Register D. The first three bits from the left may represent padding so that the value may be expressed in a 2-byte manner. The $4^{th}$ bit from the left may represent a second value, i.e. a value comparable to the 1 Hz clock signal of the system clock ripple counter. The 5th bit may represent a half second value, i.e. a value comparable to the 2 Hz single from the ripple counter, and the $6^{th}$ bit may represent a quarter second value, i.e. a value comparable to the 4 Hz clock signal from the ripple counter, and so forth. Based on these definitions a value of "0001 11XX XXXX XXXX" is within 0.25 seconds before a second boundary and a value of "0000 00XX XXXX XXXX" is within 0.25 seconds after the second mark. As such a comparison of the 11th and 12th bit values in register D (or even to register B) with 00 or 11 will indicate whether the value is within the desired range. Of course, other comparisons and selected bit values may be used for other preset tolerance amounts. As such, in this embodiment, prior to an RF one second signal being generated the value of selected bits in REG D are analyzed to determine if they meet the above criteria. This analysis may be performed in many ways such as by comparing the value of the selected bits independently to values for upper and lower limits, or in the case of the above example, by simply confirming that the 11th and 12th bits were identical.

In other alternative embodiments excess drift may be determined directly by comparing a limiting value directly to a value determined for the estimated drift prior to loading any value into REG B. In still other alternatives, the concept of limiting what drift values may be eliminated. This elimination may come at the expense of transmitting one or more additional bits of information with messages that indicate one or more attributes of transmission time (e.g. whether the transmission start on an even or odd second boundary or potentially what the second number was. Additional hardware could be added to what was described above to handle these alternatives. In other embodiments, portions of the synchronization process could be performed by software, such as processing of information related to whether the second was even or odd) and then updating registers as appropriate.

As an example, suppose that 2 minutes after receiving the synchronization message, the communication device needs to transmit a message to the implantable device. Since the known error is 24 counts per 5 minutes, the external communication device will be about 10 counts fast compared to the implantable device. If in the implantable device, a value 0x1000 is loaded into the B register, the implantable device will begin listening and/or transmitting exactly at the one second mark of the implantable device. In the external communication device, by loading the value (0x1000−0x000A) into the B register, the external communication device will begin receiving and/or transmitting 10 bit times earlier than it otherwise would and thus as it is anticipated that the external communication device's clock is actually 10 bit times ahead of the implantable device's clock the transmission and reception will be reasonably synchronized under the assumption that drift has not changed significantly.

As CNT B is updated with the value in CNT A every time a valid message is received, a current drift amount, though not drift rate, will be reset to zero upon receipt of each message.

Similarly, if the external communication device is programmed or otherwise configured to potentially receive messages from the implantable device every minute, the value in the B register may be updated each minute, so that the receiver will be listening at the appropriate times. In the first minute after synchronization, the register, for example, may be set to 0x1000 minus 0x0005; in the second minute, 0x1000 minus 0x000A, and so on.

In the present protocol, no more than one message can be received for each reception window or listening period. In alternative embodiments, a "multiple message op-code" and a "number of messages parameter", or the like, may be used such that the receiver knows that it must remain on until an indicated number of messages have been received.

As noted above, in a preferred implementation of the present embodiment, telemetry hardware is used to identify the bit sync, frame sync, and telemetry ID portions of an incoming message as opposed to using software to interrupt the initial bytes of a potential incoming message. After the hardware confirms that the incoming message is for the particular receiver, the hardware activates the CPU of the processor IC so that software can aid in receiving, interpreting, and validating the message. This allows the power consumption of the receiver to remain at a minimum level while waiting for incoming messages to be initially screened. Also as noted above, in a preferred implementation the receiver only listens for incoming messages at discreet intervals for limited periods so as to further minimize power consumption associated with maintaining communication. As it is preferred that the limited listening periods are relatively small compared to the listening intervals, it is preferred that a reasonable level of time synchronization be maintained between the transmitter and receiver so as to minimize excess power consumption and user inconvenience associated with using extended attention preambles, multiple communication attempts, or the like, to ensure appropriate information transfer is achieved.

In alternative embodiments, particularly where power consumption is less critical, the power of the microprocessor might be utilized to control the telemetry hardware during the reception of any or all of the preamble, frame sync, or telemetry ID portions of the message or may even be used to activate the reception hardware at the listening start time and to deactivate the hardware at the end of the listening period if it is determined that no message was incoming.

In a preferred time synchronization implementation, the concept of time at the second and subsecond level is dictated by the implantable device, whereas the concept of time at the minute and hour level is dictated by the external communication device. Of course, other synchronization schemes may be alternatively defined.

In the present embodiment, transmissions are allowed to begin only at the boundaries of seconds as measured by the transmitter's telemetry timer (taking into account any offsets associated with time synchronization). Selected boundaries of seconds within each minute are assigned either as a potential outbound transmission start time from the implantable device to the external communication device or as a potential inbound transmission start time from the external communication device to the implantable device. For example, each boundary at the beginning of an even second may represent a potential start time for inbound transmissions, while one or more odd second boundaries during each minute may represent potential start times for unsolicited outbound transmissions. A predefined inbound transmission start time may be replaced by transmission start time for a solicited outbound message as the external communication device is awaiting a response to the communication that solicited the response from the implantable device. In other embodiments, potential transmission times may be set to start on something other than boundaries of seconds. In still other embodiments, the communication device may continue to transmit messages based on inbound transmission start times as the implantable device may be listening only during predefined inbound listening periods, while the implantable device may be able to transmit at any time, outside of its normal predefined listening time slots, as the external communication device may be continuously listening for outbound communications any time it is not transmitting.

In the present embodiment, depending on the type of message, a 1-byte or 2-byte cyclical redundancy code (CRC) follows the data bytes. It is preferred that the CRC be generally computed using the telemetry ID of the message originator (i.e. the telemetry ID of the transmitter). This serves as a form of security. If a message with this type of CRC is received by an implantable device, the implantable device must have advanced knowledge of the telemetry ID of the transmitting external communication device or the implantable device will reject the message because of a CRC error. Similarly the communication device may simply reject messages that do not originate from its partnered medical device.

A CRC to be included with a message, in the present embodiment, is calculated based on the successive bytes forming the message and possibly upon the identity of the transmitter as well. When the CRC is computed using the telemetry ID of the message originator, the first three bytes used in the calculation are the telemetry ID of the originator. The CRC calculation then uses the three bytes of the telemetry ID of the intended receiver, the 1-byte of op-code, and then the remaining bytes of data in the message (with the exception of the CRC itself that is being calculated). When the CRC is not computed with the message originator's telemetry ID, the CRC is computed based on the bytes of the message starting with the message op-code, and continuing with the rest of the bytes in the data (with the exception of the CRC itself that is being calculated). Of course, in other embodiments, the CRC calculations may use the telemetry ID of the originator other than at the beginning of the calculation. In still other embodiments, the op-code may be left out of the CRC calculation. In still other embodiments, the order in which the components of the messages are calculated may be changed, though if different from the order presented in the message itself, recalculation of the CRC by the receiver may not be able to be performed on the fly as the message is being received as is done in the current embodiment.

In the present embodiment, it is preferred that a precalculated CRC transmission key and a precalculated CRC reception key are derived and stored so that they do not have to be calculated each time they are needed. The transmission key is a CRC derived from the byte-by-byte processing of the transmitter's three byte telemetry ID followed by the receiver's three byte telemetry ID. The reception transmission key is a CRC derived from the byte-by-byte processing of the transmitter's three byte telemetry ID followed by the receiver's three byte telemetry ID. Though these key definitions sound the same it must be remembered that the transmitting and receiving roles and devices are reversed. These keys are used as the starting points for deriving the CRC that is to be transmitted with the message and the CRC that is derived upon receipt of a message, respectively. In other embodiments other keys may be defined.

Further details about CRC generation may be found in (1) the above referenced concurrently filed U.S. Patent Application corresponding to Medical Research Docket No. USP-1079-A, (2) the "CCITT Red Book", Volume VIII, published by International Telecommunications Union, Geneva, 1986, Recommendation V.41, "Code-independent Error Control System", and (3) "C Programmer's Guide to Serial Communications", 2nd Edition, by Joe Campbell, published by SAMS Publishing, Indianapolis, Indiana, ISBN 0-672-30286-1. In particular chapter 3 of this latter book deals with errors and error detection including CRCs, while chapter 23 deals with calculation of CRCs. These books are hereby incorporated by reference herein as if set forth in full.

In a preferred implementation, the clock in the implantable device is the master clock in terms of tracking seconds within a minute and subseconds within a second. The implantable device obtains its concept of the minute number within an hour and hour within a day from the values set in the external communication device which typically correspond to the time of day at the patient's location. The values for subseconds within a second are preferably transmitted implicitly by the implantable device to the external communication device based on the implicit understanding that implantable device transmissions always start at second boundaries.

More specifically, each time the external communication device receives a transmission from the implantable device, it uses a combination of elements to calculate a difference between the external communication device clock and the implantable device clock. These elements include (1) the exact time that a certain portion of the transmission is received according to the external communication device clock, (2) knowledge that implantable device message transmission begins a known time according to the implantable device's clock, and (3) a known time difference between that portion of the transmission and the beginning of the transmission. These three elements may be used to determine any difference in time between the clocks and ultimately to resynchronize the clocks. Of course, in alternative embodiments synchronization may be implemented in other various ways.

In a preferred implementation, telemetry transmission and reception time slots begin exactly at one-second boundaries. Some time slots are unassigned while others are assigned as slots for communications that are inbound to the implantable device. During normal operation each even second, relative to the minute mark, is slotted for inbound transmissions. In a storage mode, the 0, 15, 30, and 45 second marks are slotted for inbound communications. Storage mode is a state of the implantable device where power consumption is reduced to a minimum level during periods of non-use thereby conserving battery power and thus extending the life of the implantable device. The one second mark after the roll over of each minute is assigned as a slot for unsolicited outbound messages (i.e. messages that are sent without a triggering message from the external communication device). Messages sent from the implantable device in response to external communication device communications (i.e. solicited messages) are sent out on the next available second mark. In alternative embodiments, it is apparent that other inbound and outbound slots may be defined.

Since most system communications of the present embodiment originate with the external communication device, and as a rapid response to programming commands is desired for user convenience, it is preferred that inbound slots be placed relatively close together (e.g. no more than 15 seconds apart, more preferably no more than 10 seconds apart, and even more preferably no more than 5 seconds apart, and most preferably no more than about 2 seconds apart. In order to save battery power on the external communication device, it is generally preferred that the system have relative few outbound slots so that the external communication device doesn't consume excessive power when unsolicited messages from the implantable device are not often used. In general, it is preferred that there be more predefined inbound time slots per time period than outbound time slots. Of course in alternative embodiments outbound time slots may exceed or equal the number of inbound time slots.

When the external communication device sends an inbound message that requires a response, the external communication device listens for the anticipated response from the implantable device that will be sent out on the next one second boundary. If a response is not received in a predefined period of time, the external communication device may automatically retransmit the message one or more times prior to alerting the patient of a failure to communicate.

In the present embodiment, all transmissions both inbound and outbound, and both solicited and unsolicited are sent using the same data transmission rates and the same carrier frequency. In alternative embodiments, however, data transmission rates may be varied, and carrier frequency may be varied. Such variations may be based on predefined time slot definitions so that both the implantable device and external communication device may properly vary their reception parameters in anticipation of how the other device may attempt to communicate. For example, solicited transmissions may occur at a different carrier than unsolicited transmissions or may occur using a different data transmission rate. The external communication device may transmit on inbound time slots with a first carrier frequency and first data rate, and the implantable device may transmit on outbound time slots with a second frequency or second data rate that may be different from the first frequency or first data rate. In still further embodiments, transmission reception & frequency may be user selectable if communication problems are excessive in the hope of finding a frequency with less interference.

To reduce power consumption, it is desirable to have telemetry hardware operate only during actual transmission times and during possible reception times. As such, the hardware, as discussed above, is configured and controlled so that this result is achieved. As power conservation in the implantable device is more critical than power conservation in the external communication device, this first embodiment places the burden associated with synchronization activities and activities associated with reestablishing synchronization, once it is lost, onto the external communication device. This desire to minimize power drain in the implantable device is balanced with a desire to have the implantable device respond quickly to commands transmitted by the external communication device. Once a command is issued by the external communication device, it is preferred, for user/patient convenience, that the implantable device receive and acknowledge the command as quickly as possible. To this end, the implantable device is provided with closely spaced reception slots (i.e. inbound listening intervals, e.g. every 2 seconds) so that communication can occur with a sufficiently fast response. Each inbound listening period, however, is of very short duration so that power consumption in the implantable device is minimized.

The duration of each inbound listening period is preferably not so small that slight variations in synchronization cause lost of reception, which would cause a delay in communication, as well as potentially causing extra power consumption in order to reestablish communication as the reception hardware may be forced to remain on for extended periods of time due to the reception of lengthy attention preambles. As such, in the present embodiment the reception time slots are turned on for an initial period of about 2–8 milliseconds (e.g. 4 milliseconds) while using an 8 kHz data transmission rate with a minimum number of 8-bit transitions necessary for establishing bit synchronization.

In alternative embodiments longer or shorter windows may be used. Relative to the incoming bit rate, it is preferred that the window remain open in the range of about one and one-half to four times the period necessary to establish bit sync and receive a complete frame sync signal.

In other alternative embodiments, if attention preamble is sent, the window may be opened only for a period necessary to establish receipt of the attention preamble and thereafter, frame sync and a valid telemetry ID may be looked for. In this alternative, to enhance likelihood of reception, the transmitter preferably does not begin transmission at what it believes is the most likely time that the receiver begins listening, but instead begins transmission at a somewhat earlier time with an attention preamble of sufficient length to cover or at least sufficiently overlap the anticipated listening period.

In the present embodiment, the implantable device always starts a transmission exactly at (an outbound transmission start time which corresponds to a second boundary) according to its own clock. The external communication device may activate its receiver at what it believes is the implantable device's outbound transmission start time based on use of any synchronization parameters established in conjunction with the previous communication(s). The external communication device may leave its reception window open for a predefined minimum period of time or alternatively it may adjust the listening period based on one or more parameters. The receiver may use one or more additional parameters to adjust the opening of the reception window to somewhat earlier than what it believes the actual start of the potential transmission is to be. This early opening of the reception window may be based on an anticipation that a certain amount of increasing uncertainty exists in the validity of the previously established synchronization and associated previously established drift parameters. In other words, this may be done in recognition that there is a tolerance around which synchronization may be drifting. Such additional parameters may also be used to lengthen the reception window beyond a predefined initial listening period.

In this embodiment, the implantable device always turns on its receiver exactly at the beginning of an inbound reception time slot. As such, if the external communication device has a message to transmit to the implantable device during that reception time slot, the external communication device may start transmitting at what it believes is the beginning of the time slot based on an estimated amount of drift that may have occurred. Alternatively, it may begin transmitting somewhat ahead of its best estimate as to when the time slot will open, in anticipation that there is some degree of uncertainty in the actual amount of drift that has occurred between its measure of time and that of the Implantable Device. In this regard, the external communication device may use an extended preamble, possibly of the standard pattern if not extended too long, but more preferably of the attention pattern so the chance of establishing communication is increased due to the receiver's attribute of having its attention held (i.e. reception hardware retained in an active state) by a communication that consists of the attention preamble pattern. The parameter used in causing the window to open early may be a fixed parameter, or a parameter that is based, at least in part, on the time difference between the present time and the time of last establishing synchronization and possibly based on an estimate of maximum likely drift rate or based on an actual amount of drift experienced between the last two communications or between several communication or associated with an amount or amounts of drift experienced during approximately the same time periods during one or more previous days. Similarly, the parameter used to extend the length of the standard preamble or attention preamble, or even to select between them, may be a fixed parameter, a parameter that is based, at least in part, on the time difference between the present time and the time of last establishing synchronization or a parameter with a different basis.

If it is determined that resynchronization is needed, the external communication device may establish re-synchronization in one of several ways. The external communication device may transmit a message with an extended preamble consisting of the attention preamble. This process may be done as a single step or it may be done in multiple steps. In the single step process, the attention preamble is set to a length of time equal to or somewhat greater than the length of time between inbound listening intervals. This message is preferably a sync message as will be discussed hereafter though it may be also be a different message. After transmission of the message, the external communication device leaves its receiver open for at least about 1–2 seconds in anticipation of the implantable device sending an outbound response. The timing of the sync response message, as well as its content, will provide the information necessary to reestablish synchronization The sync message is preferred over other messages because other messages may not carry as much information about timing between the implantable device and the external communication device as is carried by the sync message. For example, all response messages may be used to reestablish synchronization of the second boundaries, but not all messages necessarily carry sufficient information to reestablish even versus odd second boundaries or information necessary to reestablish one-minute boundaries.

In one variation of this one step process, the external communication device begins transmission of the message somewhat after its best estimate (if it has one) as to when the reception window on the implantable device will be closing. In this variation, it is hoped that the implantable device's receiver will open its reception window towards the end of transmission of the attention preamble, as opposed to toward the beginning of transmission, so that power consumption by the implantable device is minimized.

One potential multi-step process is similar to the one step process discussed above, but the first one or more attempts to establish synchronization use an attention preamble that is shorter than the inbound listening interval. In this regard, if the transmission catches the window, the receiver of the implantable device may be held open for a shorter period of time than that resulting from the one step process and thus a power savings in the implantable device may be achieved. However, if the transmission is not received, one or more subsequent messages will need to be sent, with the associated inconvenience of an extra time delay. In this process, the first message is preferably centered around the external communication device's best estimate as to inbound listening period. If communication and synchronization are not reestablished in response to the first message, one or more subsequent messages may be transmitted with longer attention preambles that still may be shorter than the interval between inbound time slots, equal to it, or even greater than it. In any event, if communication and synchronization are not reestablished using the previous attempts, a final message will be sent with an attention preamble of length equal to or greater than the inbound listening interval. If communication hasn't been reestablished based on transmitting attention preamble for a period of time equal to or somewhat greater than the normal operation inbound listening interval, it may be appropriate to send an attention preamble for a time period equal to or somewhat greater than the storage mode inbound listening interval as the system may have inadvertently been shifted to that mode. If communication is still not established, the patient may be alerted to the problem so that he/she may reposition the external communication device relative to the implantable device, go to a different location where electromagnetic interference may be reduced, or otherwise seek assistance in addressing the problem.

As a second example of a potential multistep synchronization process the length of the attention preamble may not be increased beyond that selected for the first attempt, instead if multiple attempts are needed, the start time of transmission may be shifted such that the entire set of messages, if required to be sent, will cover all possible portions of the inbound listening interval by covering a different portion of each interval in a series of intervals.

As a further alternative, if unsolicited communications are outbound from the implantable device on a periodic basis, the external communication device may simply open its reception window for the entire interval between at least two of the successive periodic outbound communications so the message known to be transmitted sometime during the interval will be received assuming that the devices are within telemetry range and other problems are not present such that synchronization may be reestablished.

Some messages may be transmitted without expecting a response, in which case the sender will not know whether they were correctly received (non-response transactions). Other messages may require a response. If a response to these messages is not received, the transmitter will respond to the failure by repeating transmission of the message. After a predefined number of transmission attempts without a response, the message may be declared undeliverable, and the patient may be alerted to the problem. In the present embodiment, status messages do not require a response.

All messages (with the exception of the link message and the interrogate message) that require a response and trigger an action in the receiver, and all responses to such messages, are transmitted with a sequence number. In the present embodiment, that sequence number is a single bit that identifies the sequence of messages. As such, this sequence number is toggled between its two possible states "1" and "0", by the transmitter each time a message is sent and the appropriate response (including the sequence number) is received. The receiver toggles its concept of what the sequence number should be when it receives a valid message with the sequence number that it is next expecting. If it receives a message with a sequence number it is not expecting, it sends a response indicating that the message was received but does not act upon the content in the message. In alternative embodiments, the sequence numbering may be removed or enhanced to include more than one bit. The sequence number is used to ensure that a given message is only acted upon once, though the message may be received multiple times and multiple responses sent out. This situation may occur when the sender does not receive the response and then automatically resends the message one or more times. If a response is not received after one or more attempted retransmissions, the synchronization process is attempted. If that fails, the patient is alerted to the condition so that subsequent steps may be taken. In any event, once communication is reestablished, the message is resent and an appropriate response looked for. If the original message was not received in the original transmission attempts, and was only received in the last transmission attempt, and it dealt with an insulin delivery issue that was not longer applicable, the delivery could be canceled by going into a suspend mode or by taking other steps in a timely manner. Suspend mode is an operational state of the implantable device where insulin delivery is reduced to a medically insignificant level.

If a received message requires a response, the recipient responds during the next available transmission period. If a received message has an incorrect CRC, it is ignored. In the present embodiment, the sender of a messages waits a predetermined period of time for the anticipated response message and if it does not receive the response as expected, it takes the appropriate course of action as noted above.

The user may need to change the time defined in the external communication device. This may result from changes when traveling between time zones, due to annual shifts in time, as well as due to slight errors in tracking time. In the present embodiment, the external communication device keeps track of minutes, hours, and days based on the operation of its clock and any updates from a user. The external communication device receives it concept of seconds within a minute from that found in the implantable device and as such does not allow user input to update a second value. The external communication device does not track seconds within minutes. When the user changes the time on the external communication device, an appropriate message is transmitted to the implantable device so that it may adapt to the new time of day. This is done because certain automatic delivery regimes (e.g. basal rate profiles) are based on the time of day. In the present embodiment, delivery is not automatically changed between various days of the week or month and as such the implantable device has no need of tracking this information. However, if in alternative embodiments day sensitive delivery routines are implemented in an automated manner then the external communication device could be programmed to pass this information to the implantable device which may be programmed to accept and use it. If it is found desirable for the communication device to track seconds, in an alternative embodiment, the medical device could obtain its concept of seconds from the communication device.

In some embodiments, software may be downloaded from the external communication device to the implantable device. The downloading of software may include the downloading of executable software as well as the downloading of data structures that may be used by the executable software.

In the present embodiment, a specific external communication device is configured/programmed to communicate substantively with only one specific implantable device, that is in turn configured/programmed to communicate substantively with only the same specific external communication device. An external communication device is capable of retaining the telemetry ID of exactly one implantable device at a time and an implantable device is capable of retaining the telemetry ID of exactly one external communication device at a time. A small amount of non-substantive communication (i.e. communication that does not impact insulin delivery) can occur between external communication devices and implantable devices that are not linked (i.e. partnered or married) to one another (i.e. provided with each others telemetry IDs). Only communications between linked devices are used in the time synchronization process.

In the present embodiment, many different types of messages and responses thereto can be written into the programs that control the implantable device and the external communication device according to the protocol features set forth above. These messages may be used for a number of different purposes. For example, (1) they may be system level messages that are used for testing devices, for resetting devices, or for establishing relationships between implantable devices and external communication devices, (2) they may be alarm messages that are used to convey alarm conditions or to clear alarm conditions, (3) they may be miscellaneous messages that set various parameters or perform various read operations, (4) they may be delivery messages that set delivery amounts, read delivery status, or set parameters such as concentration and pump stroke volume that may be required to appropriately control delivery of the drug, (5) they may be data log messages that set data log boundaries, read boundaries, or clear data logs, boundaries or read information from various data logs or supply information to those data logs, (6) they may be refill messages that are related to amounts of material that are added to the reservoir periodically, (7) they may be compound messages that perform more than one function, or (8) they may be error messages that request error condition status or supply error condition status. In other embodiments, messages may be classified in different ways.

Various the features of the above embodiment and its alternatives provide enhanced accuracy of timers, ability to transmit and receive messages in target time periods, ability to accurately synchronize the time periods so that communication can occur with little inconvenience to the user and with little waste of power, ability to recover from a loss of synchronization in an power and/or time efficient manner, and/or ability to reduce power consumption. These improvement provide more robust, effective, reliable, and safe operation of an implantable medical device and more generically for an ambulatory medical device.

While the above embodiment has primarily been concerned with an implantable infusion pump that dispenses insulin using a piston type pump mechanism, the telemetry and timing features disclosed herein may be used in other ambulatory devices such as implantable pacemakers, defibrillators, other implantable tissue stimulators, implantable physiologic sensors such as electrochemical oxygen sensors, peroxide sensors, or enzymatic sensors such as glucose sensors, externally carried infusion pumps, implantable infusion pumps that use other pumping mechanisms or simply used excess pressure and controlled flow elements to infuse various medications and drugs such as analgesics, drugs for treating AIDS, drugs for treating psychological disorders and the like. For example, the telemetry features presented above may be used with an external infusion pump that may or may not have a built in display and keypad but is equipped with a telemetry system that can communicate with a physically separated communication device so that the pump need not be accessed in order to provide commands to it and receive data from it.

In these various alternatives, the physical, electronic, and programmed features of the communication device and implantable device may have different components and features than presented above for the implantable pump system so that their desired medical functionality and safety requirements are achieved and such that appropriate control and feedback is provided between the medical device and its communication device.

In other alternative embodiments the medical device may include two medical devices such as an implantable pump and an implantable sensor. The pump may dispense a drug whose physiological impact on the body (e.g. analgesic impact) is ascertained by the sensor or alternatively the sensor may supply a physiological reading that indicates a need for infusion of the drug. The pump may operate in a closed loop manner with the sensor or it may operate in an open loop manner where the patient is required to interpret sensor output information and is required to issue appropriate infusion commands to the pump. For example, in the case of a diabetic patient, the drug may be insulin and the sensor may detect glucose level.

In other alternative embodiments two medical devices may be implanted adjacent one another or at an extended distance from one another. If not placed in physical contact with one another, a lead may be used to provide power conduction from one device to the other and also be used to conduct communication signals between the devices. Alternatively, each device may include at least one telemetry system that allows direct communication between each or allows indirect communication to occur via the external communication device or other external device. Each device may be supplied with its own power supply. Depending on the communication requirements each device may use two way communication (i.e. both outbound and inbound communication) or allow only one way communication (i.e. outbound communication or possibly inbound communication).

In other alternatives, both the medical device and the communication device may be external devices (e.g. an external pump and an external RF telemetry based communication device). In still further alternatives, a first type of medical device may be implanted (e.g. an infusion pump or a sensor) while a second medical device may be external (e.g. the opposite of a sensor or an infusion pump). Where at least one of the medical devices is external, it may also function as the communication device for the other medical device in which case it may possess a display for providing information to the patient and a keypad for allowing entry of commands for issuance to the implantable device as well as for direct use by itself. Even if at least one of the medical devices is external, it may be inconvenient to access that device when information is needed or commands must be given, as such an external, non-medical communication device may be supplied that has information output (e.g. display) capabilities and input (e.g. keypad) capabilities. If a separate communication device is provided, the external medical device may or may not have display and input capabilities.

The telemetry features presented above may be used with various forms of distant communication (e.g. between the implantable device and other external devices or between the external communication device and other external devices). For example communication may occur via various electromagnetic links like IR, optical links, longer or shorter wavelength RF, audio links, ultrasonic links, acoustic links, inductive links, and the like. Various telemetry systems may be used. Telemetry systems may be of the analog type, digital type, or mixed.

The various telemetry and timing features presented above may be used in various combinations be used separately to enhance communications between ambulatory medical devices and communication devices and/or controllers associated therewith.

In other embodiments two independent processors may be used that operate from a single timing chain. In these alternatives, it is preferable that at least one of the timing signals (e.g. one of the lower frequency timers) be monitored by an independently timed watchdog circuit to reduce the risk of timing problems going undetected.

In still additional embodiments, an implantable glucose sensor may be used in conjunction with an implantable insulin pump to provide feedback to the patient or physician on the effectiveness of the insulin delivery system. The patient could use the feedback to assist in making insulin delivery decisions in an open loop manner. Alternatively, the operation of the pump could be tied to the sensor output in a more or less closed loop manner to give a more automated character to system operation. Insulin may be infused without any user intervention, without pre-delivery information, and even without direct post delivery feedback. In a less automated closed loop system, drug infusion recommendations could be derived by the system and presented to the user before delivery or the system could require user acknowledgment prior to proceeding with delivery for amounts or rates exceed a predefined limit. The implantable sensor may have its own power supply or may receive power from the control circuitry provided within the pump housing through a physical lead that connects them. Power may be supplied through one or more independent leads or alternatively may be transferred over one or more data lines through the communication signals themselves. Communication may be exchanged in various ways including, for example, via galvanic leads, RF telemetry, fiber optics, and the like, and may be of digital, analog, or combined form. The sensor system may include a plurality of sensor elements which might allow continued glucose data to be supplied even though some portion of the sensors stop operating, lose calibration or produce questionable readings. The most preferred sensors would include electronic processing capability in the form of an integrated circuit mounted in or forming a part of a housing for the sensor. This configuration has the advantage of allowing digital communications between the physical sensor and any separated electronic control module.

Further teachings concerning implantable sensors and implantable sensor systems are found in a number of patents issued to D. A. Gough, including (1) U.S. Pat. No. 4,484,987, entitled "Method And Membrane Applicable To Implantable Sensor"; (2) U.S. Pat. No. 4,627,906, entitled "Electrochemical Sensor Having Improved Stability"; (3) U.S. Pat. No. 4,671,288, entitled "Electrochemical Cell Sensor For Continuous Short-Term Use In Tissues And Blood"; (4) U.S. Pat. No. 4,703,756, entitled "Complete Glucose Monitoring System With An Implantable Telemetered Sensor Module"; and (5) U.S. Pat. No. 4,781,798, entitled "Transparent Multi-Oxygen Sensor Array And Method Of Using Same". Each of these patents is incorporated herein by reference as if set forth in full.

Still further teachings concerning implantable sensors and sensor systems are found in a number of patents issued to J. H. Schulman, et al., including (1) U.S. Pat. No. 5,497,772, entitled "Glucose Monitoring System"; (2) U.S. Pat. No. 5,651,767, entitled "Replaceable Catheter System for Physiological Sensors, Stimulating Electrodes and/or Implantable Fluid Delivery Systems"; (3) U.S. Pat. No. 5,750,926, entitled "Hermetically Sealed Electrical Feedthrough For Use With Implantable Electronic Devices"; (4) U.S. Pat. No. 6,043,437, entitled "Alumina Insulation for Coating Implantable Components and Other Microminiature Devices"; (5) U.S. Pat. No. 6,088,608, entitled "Implantable Sensor and Integrity Test Therefor"; and (6) U.S. Pat. No. 6,119,028, entitled "Implantable Enzyme-Based Monitoring Systems Having Improved Longevity Due to Improved Exterior Surfaces". Each of these patents is incorporated herein by reference as if set forth in full.

Additional further teachings concerning implantable sensors and sensor systems are found in (1) U.S. Pat. No. 5,917,346, issued to J. C. Gord, et al., and entitled "Low power current-to-frequency converter"; (2) U.S. Pat. No. 5,999,848, issued to J. C. Gord, and entitled "Daisy Chainable Sensors for Implantation in Living Tissue"; (3) U.S. Pat. No. 5,999,849, issued to L. D. Canfield, et al., and entitled "Low Power Rectifier Circuit for Implantable Medical Devices"; and (4) U.S. Pat. No. 6,081,736, issued to M. S. Colvin, et al., and entitled "Implantable Enzyme-Based Monitoring Systems Adapted for Long Term Use". Each of these patents is incorporated herein by reference as if set forth in full.

Further teachings concerning implantable infusion pumps are found in a number of patents by R. E. Fischell, including (1) U.S. Pat. No. 4,373,527, entitled "Implantable, Programmable Medication Infusion System"; (2) U.S. Pat. No. 4,494,950, entitled "Infusion Device Intended for Implantation in a Living Body"; (3) U.S. Pat. No. 4,525,165, entitled "Fluid Handling System for Medication Infusion System"; (4) U.S. Pat. No. 4,573,994, entitled "Refillable Medication Infusion Apparatus"; (5) U.S. Pat. No. 4,594,058, entitled "Single Valve Diaphragm Pump with Decreased Sensitivity to Ambient Conditions"; (6) U.S. Pat. No. 4,619,653, entitled "Apparatus For Detecting At Least One Predetermined Condition And Providing An Informational Signal In Response Thereto In A Medication Infusion System"; (7) U.S. Pat. No. 4,661,097, entitled "Method for Clearing a Gas Bubble From a Positive Displacement Pump Contained Within a Fluid Dispensing System"; (8) U.S. Pat. No. 4,731,051, entitled "Programmable Control Means for Providing Safe and Controlled Medication Infusion"; and (9) U.S. Pat. No. 4,784,645, entitled, "Apparatus For Detecting A Condition Of A Medication Infusion System And Providing An Informational Signal In Response Thereto". Each of these patents is incorporated herein by reference as if set forth in full.

Still further teachings concerning infusion pumps are found in a number of patents by Franetzki, including (1) U.S. Pat. No. 4,191,181, entitled "Apparatus For Infusion of Liquids", (2) U.S. Pat. No. 4,217,894, entitled "Apparatus for Supplying Medication to the Human or Animal Body"; (3) U.S. Pat. No. 4,270,532, entitled "Device for the Pre-programmable Infusion of Liquids"; (4) U.S. Pat. No. 4,282,872, entitled "Device for the Pre-programmable Infusion of Liquids", U.S. Pat. No. 4,373,527, entitled "Implantable, Programmable Medication Infusion System"; (5) U.S. Pat. No. 4,511,355, entitled "Plural Module Medication Delivery System", (6) U.S. Pat. No. 4,559,037, entitled "Device for the Pre-programmable Infusion of Liquids"; (7) U.S. Pat. No. 4,776,842, entitled "Device for the Administration of Medications". Each of these patents is incorporated herein by reference as if set forth in full.

Teachings concerning tissue stimulators are found in a number of patents by J. H. Schulman, including (1) U.S. Pat. No. 5,193,539, entitled "Implantable microstimulator"; (2) U.S. Pat. No. 5,193,540; entitled "Structure and Method of Manufacture of an Implantable Microstimulator"; and (3) U.S. Pat. No. 5,358,514, entitled "Implantable Microdevices with Self Attaching Electrodes". Further teachings are also found in (1) U.S. Pat. No. 5,957,958, by Loeb et al., entitled "Implantable nerve or muscle stimulator e.g. a cochlear prosthesis", in (2) U.S. Pat. No. 5,571,148, by G. E. Loeb, et al., entitled "Implantable Multichannel Stimulator"; and in (3) PCT Publication No. WO 00/74751, by A. E. Mann, and entitled "Method and Apparatus for Infusing Liquids Using a Chemical Reaction in an Implanted Infusion Device". Each of these publications is incorporated herein by reference as if set forth in full.

The control of an implantable sensor could be provided through the functionality of one or both Processor ICs. One Processor IC could supply power and/or control signals to the sensor(s) and receive data back from the sensor, while the other processor could monitor the activity to ensure that sensor activity meets certain predefined guidelines.

In other embodiments, the External Communication Device of the first embodiment could be functionally linked to an external glucose sensor system such as the continuous glucose monitoring system (CGMS) offered by Minimed Inc. of Northridge, Calif. The link may be established, for example, through a physical lead or by RF telemetry.

In other embodiments other implantable, or external, sensor systems that measure something other than glucose could also be functionally coupled to the implantable device either to receive power and/or to provide data. Other such sensors might include oxygen sensors, peroxide sensors, pulse rate sensors, temperature sensors, accelerometers, and the like.

In still other alternative embodiments, the electronic control system of the first embodiment could be configured to control one or more implantable sensors or electrical stimulators with or without infusion functionality incorporated into the implantable device.

Further embodiments will be apparent to those of skill in the art upon review of the disclosure provided herein. Still further embodiments may be derived from the teachings set forth explicitly herein in combination with the teachings found in the various patent applications.

While the description herein sets forth particular embodiments, it is believed that those of skill in the art will recognize many variations to the presented embodiments based on the teachings herein, as such it is believed that many additional modifications may be made without departing from the spirit of the teachings herein. The accompanying claims are intended to cover such modifications as would fall within the true scope and spirit of the present invention.

The disclosed embodiments are therefore to be considered as illustrative and not necessarily restrictive, the scope of the invention being indicated by the appended claims, rather than the foregoing description, and all changes which come within the meaning and range of equivalency of the claims are therefore intended to be embraced therein.

We claim:

1. A medical system, comprising:
   a) an ambulatory medical device (MD) comprising MD electronic control circuitry that further comprises at least one MD telemetry system and at least one MD processor that controls, at least in part, operation of the MD telemetry system and operation of the medical device, wherein the medical device is configured to provide a treatment to a body of a patient or to monitor a selected state of the body;
   b) a communication device (CD) comprising CD electronic control circuitry that further comprises at least one CD telemetry system and at least one CD processor that controls, at least in part, operation of the CD telemetry system and operation of the communication device, wherein the CD telemetry system sends messages to or receives messages from the MD telemetry system; and
   c) a pulse stealer circuit wherein the pulse stealer circuit removes a single pulse from an input clock signal having a first frequency at a predefined repetition rate so as to modify the input clock signal from the first frequency to a second frequency,
   wherein the MD telemetry system and the CD telemetry system send and receive messages using digital modulation and demodulation.

2. The system of claim 1 wherein a first portion of the MD telemetry system is incorporated into the MD processor and a second portion of the MD telemetry system is external to the MD processor, or wherein a first portion of the CD telemetry system is incorporated into the CD processor and a second portion of the CD telemetry system is external to the CD processor.

3. The system of claim 2 wherein (1) the MD electronic control circuitry comprises at least one external MD functional module, other than the second portion of the MD telemetry system, that is external to the MD processor, (2) the CD electronic control circuitry comprises at least one external CD functional module, other than the second portion of the CD telemetry system, that is external to the CD processor, (3) the MD processor comprises an internal MD CPU and at least one other internal MD functional module, or (4) the CD processor comprises an internal CD CPU and at least one other internal CD functional module.

4. The system of claim 1 wherein the digital modulation and demodulation uses spread spectrum technology.

5. The system of claim 1 wherein the medical device only listens for messages coming from the communication device during prescribed inbound listening periods at selected times.

6. The system of claim 1 wherein the MD telemetry system comprises: (1) a digital modulator, (2) a receiving amplifier, (3) a digital receiver, (4) a mixer, and (5) a low pass filter wherein at least two of (1)–(5) are combined into a single integrated circuit.

7. The system of claim 1 wherein the MD telemetry system comprises: (1) a digital modulator, (2) a receiving amplifier, (3) a digital receiver, (4) a mixer, and (5) a low pass filter wherein all of (1)–(5) are combined into no more than two integrated circuits.

8. The system of claim 1 wherein the timing for the telemetry reception and transmission by the MD telemetry system and CD telemetry system are based on time periods derived from the pulse stealer circuit.

9. A medical system, comprising
   a) an ambulatory medical device (MD) comprising MD electronic control circuitry that further comprises at least one MD telemetry system and at least one MD processor that controls, at least in part, operation of the MD telemetry system and operation of the medical device, wherein the medical device is configured to provide a treatment to a body of a patient or to monitor a selected state of the body;
   b) a communication device (CD) comprising CD electronic control circuitry that further comprises at least one CD telemetry system and at least one CD processor that controls, at least in part, operation of the CD telemetry system and operation of the communication device, wherein the CD telemetry system sends messages to or receives messages from the MD telemetry system,
   wherein the MD telemetry system and the CD telemetry system send and receive messages using digital modulation and demodulation; and
   wherein the messages are quadrature phase modulated.

10. The system of claim 9 wherein the messages are sent simultaneously with in phase and quadrature phase components.

11. The system of claim 10 wherein both in phase and quadrature phase components are used in the demodulation of the message to derive the transmitted data and a reference clock signal.

12. The system of claim 11 wherein the data transfer rate is greater than 1K baud.

13. The system of claim 12 wherein the data transfer rate is greater than 4K baud.

14. The system of claim 13 wherein the data transfer is 8K baud +/−1 K baud.

15. The system of claim 1 wherein the communications are transferred on a carrier frequency of between 50 kHz and 500 kHz.

16. The system of claim 15 wherein the frequency is between 100 kHz and 400 kHz.

17. The system of claim 16 wherein the frequency is between 120 kHz and 300 kHz.

* * * * *